United States Patent
Höfer et al.

(10) Patent No.: US 9,121,026 B2
(45) Date of Patent: Sep. 1, 2015

(54) YEAST STRAIN AND SCREENING METHOD FOR IDENTIFYING INHIBITORS OF THE EXPRESSION OF THE HEXOSE TRANSPORTER GENES BY A POSITIVE PHENOTYPE

(75) Inventors: Milan Höfer, Meckenheim (DE); Jost Ludwig, Remagen (DE); Petra Schwanewilm, Niederzier (DE); Julius Subik, Bartislava (SK)

(73) Assignees: Milan Hofer, Meckenheim (DE); The South Bohemian University, Ceske Budejovice (CZ)

( * ) Notice: Subject to any disclaimer, the term of this patent is extended or adjusted under 35 U.S.C. 154(b) by 1689 days.

(21) Appl. No.: 11/791,704

(22) PCT Filed: Nov. 25, 2005

(86) PCT No.: PCT/EP2005/056216
§ 371 (c)(1),
(2), (4) Date: Feb. 19, 2008

(87) PCT Pub. No.: WO2006/056597
PCT Pub. Date: Jun. 1, 2006

(65) Prior Publication Data
US 2009/0035755 A1    Feb. 5, 2009

(30) Foreign Application Priority Data
Nov. 29, 2004 (EP) .................... 04106160

(51) Int. Cl.
*C12N 15/81* (2006.01)
*C07K 14/39* (2006.01)
*C07H 21/02* (2006.01)

(52) U.S. Cl.
CPC ............... *C12N 15/81* (2013.01); *C07K 14/39* (2013.01)

(58) Field of Classification Search
None
See application file for complete search history.

(56) References Cited

U.S. PATENT DOCUMENTS 6,589,773 B1 * 7/2003 Khazak .................... 435/254.21

OTHER PUBLICATIONS

Kozovska Z, Hikkel I, Sidorova M, Subik J. Yeast strains designed for screening of reversal agents and genetic suppresors of multidrug resistance. Int J Antimicrob Agents. Oct. 2004;24(4):386-92.
Sedlak, Miroslav et al. "Characterization of the effectivenss of hexose transporters for transporting xylose during glucose and xylose co-fermentation by a recombinant *Saccharomyces* Yeast" *Yeast* 21(8):671-784 (Jun. 2004).

* cited by examiner

*Primary Examiner* — Nancy T Vogel
(74) *Attorney, Agent, or Firm* — Ballard Spahr LLP

(57) ABSTRACT

The present invention provides screening procedures for identifying inhibitors of components of regulatory networks by a positive phenotype and modified yeast cell lines suitable for said screening. The screening procedures are especially suited to screen for substances that re-sensitize resistant pathogenic microorganisms or tumor cells by suspending the expression of resistance-relevant genes. The invention further provides methods for constructing said cell lines and their use in screening systems.

21 Claims, 17 Drawing Sheets

A

B

YEAST STRAIN AND SCREENING METHOD FOR IDENTIFYING INHIBITORS OF THE EXPRESSION OF THE HEXOSE TRANSPORTER GENES BY A POSITIVE PHENOTYPE

CROSS REFERENCE TO RELATED APPLICATIONS

The present application is a National Phase Application of International Application No. PCT/EP2005/056216, filed Nov. 25, 2005, which claims priority to European Patent Application No. 04106160.7 filed Nov. 29, 2004, which applications are incorporated herein fully by this reference.

The present invention provides screening procedures for identifying inhibitors of components of regulatory networks by a positive phenotype and modified yeast cell lines suitable for said screening. The screening procedures are especially suited to screen for substances that re-sensitize resistant pathogenic microorganisms or tumor cells by suspending the expression of resistance-relevant genes. The invention further provides methods for constructing said cell lines and their use in screening systems.

BACKGROUND

Multiple drug resistance (MDR) has become an increasing problem in clinical therapy. Especially immuno-compromised persons suffer from severe secondary infections with multi resistant pathogens during hospital treatment. Prevalent are infections with the pathogenic yeasts of the genus Candida. In addition to secondary infections, MDR is a spreading problem in cancer chemotherapy, as cancerous cells are also developing MDR to chemotherapeutics. Both types of MDR are mainly caused by drug exporting transporters with a very broad substrate specificity, making the chemical treatment inefficient. The laborious development of new antibiotics and chemotherapeutics does not really solve the problem as the cells quickly gain resistance to the new drug. In the presence of drugs, the genes coding for the drug transporters are exceedingly expressed. This leads to a quick outward transport of the drugs that thus cannot reach their targets inside the cells anymore.

MDR is frequently due to the altered expression of an ATP-binding cassette (ABC) transporter (Wadkins, R. M. et al., Intl. Rev. Cytology 171:121-165 (1997)). Over one hundred ABC transporters have been identified in species ranging from *Escherichia coli* to humans (Higgins, C. F., Cell 82:693-696 (1995)). Prominent representatives of MDR pumps conferring multidrug resistance are in *Saccharomyces cerevisiae* Pdr5p, Snq2p, Yor1p (Balzi, E. et al., Journal of Biological Chemistry 269:2206-2214 (1994); Decottignies, A. et al., Journal of Biological Chemistry, 270:18150-18157 (1995); Katzmann, D. J. et al., Molecular and Cellular Biology, 15:6875-6883 (1995); Servos, J. et al., Molecular and General Genetics 236: 214-218 (1993)) in *Candida albicans* Cdr1p and Cdr2p (Prasad, R. et al., Current Genetics 4:320-329 (1995); Sanglard, D. et al., Microbiology 143:405-516 (1997)) and in *Homo sapiens* P-glycoprotein (Pgp) Mdr1 (Ueda, K. et al., Journal of Biological Chemistry 262:505-508 (1987)). Pdr5p is part of the well known multiple drug resistance (MDR) network of *S. cerevisiae* (also called pleiotropic drug resistance, PDR). Pgp provides one mechanism of possibly inhibiting resistance in tumor cells to chemotherapeutic agents (Senior, A. E. et al., FEBS Letters, 377:285-289 (1995); Abraham, E. H. et al., Proc. Natl. Acad. Sci. USA 90:312-316 (1993)).

To abolish this phenomenon and block these pumps, most recently inhibitors of these membrane proteins are provided in combination with antibiotics and chemotherapeutics. However, the inhibitors themselves become substrates of the pumps and thus, loose their inhibitory effect (Maki, N. et al., The Journal of Biological Chemistry 278:18132-18139 (2003); Smith, A. J. et al., Journal of the Natural Cancer Institute 90:1161-1166 (1998)).

An alternative approach, which underlies the present invention and which should solve these problems in therapy, is to inhibit the expression of the transporter genes. When the expression of the pump genes is suspended the therapeutics cannot be transported out of the cells. The inhibition of the expression can occur at different steps in the regulatory network, e.g. at the promoter level of the transporter genes, at the level of transcription factor(s) of the promoters or even at the promoter level of the transcription factor(s). In consequence, inhibition of any element of the MDR regulatory network would lead to (re)sensitised formerly resistant cells. Applying such an inhibitory substance in combination with not any more effective antibiotics or chemotherapeutics would restore their antibiotic or chemotherapeutic effect in currently resistant pathogens or tumour cells, respectively.

However, a reliable system to identify substances that specifically inhibit transcription factors and/or their promoters as well as the target promoters is not available. Especially, no technique is known which would enable to screen for such substances in a one-step-procedure.

Most of the known screening systems for regulatory effectors have been based on measuring the activity of the respective promoters by using appropriate reporter genes, e.g. coding for the green fluorescent protein (GFP) (Chalfie, M. et al., Science 263:802-805 (1994); Cormack, B. P. et al., Microbiology 143:303-311 (1997); Wiesner, C. et al., Nucleic Acids Research 80:e80 (2002); Barelle, C. J. et al., Yeast 21:333-340 (2004)), for the β-galactosidase (Leuker, C. E. et al., Molecular Genetics and Genomics 235:235-241 (1992)) or for the luciferase (Bronstein, I. et al., Analytical Biochemistry 219:169-181 (1994); Vieeites, J. M. et al., Yeast 10:1321-1327 (1994); Srikantha, T. et al., Journal of Bacteriology 178:121-129 (1996); Leskinen, P. et al., Yeast 20:1109-1113 (2003)). To measure the activity of promoters the micro-array technique has been prevailing (Wolfsberg, T. G. et al., Genome Research 8:775-792 (1999); Devaux, F. et al., FEBS Letters 498:140-144 (2001); Hikkel, I. et al., The Journal of Biological Chemistry 278:11427-11432 (2003); Li, T. et al., Circulation Research 93:1202-1209 (2003)). A common characteristic of all of these systems and methods is that the inhibition of the transcription results in a negative phenotype and that the quantification of the phenotype requires individual measurements. A negative phenotype does not necessarily result from inhibition of the expression of the reporter gene but can also result from an unspecific metabolic inhibition within the cell. The above mentioned screening systems can not distinguish between specific inhibition of the regulatory network or unspecific metabolic inhibition.

One screening system (Kozovská, Z. et al., Int. J. Antimicrobial Agents 22:284-290 (2003); Kozowska, Z. et al., Int. J. Antimicrob. Agents 24:386-392 (2004)) is based on a dominant lethal reporter gene that allows to distinguish between a specific and an unspecific inhibition. The reporter gene is expressed under the control of the promoter of a MDR conferring gene, which in turn is under control of a transcription factor, the expression of which is inducible. Only the inhibition of the promoter (or the gene product itself) allows for growth of the cell. In this respect, unspecific metabolic inhibition is not detected by the system as it would also not allow cell growth. Unfortunately, expression of the reporter gene is lethal for the cell. Thus, cloning of the test strain is very difficult. It is only possible if the reporter gene is not expressed and thus, the lethal gene product not present in the cell. This also explains the elaborate promoter construct. The choice of promoters to be screened is limited to those that have no (or very low) basal activity and are controlled by transcription factors. However, some of the genes conferring MDR possess very active promoters. For example, the CDR1 gene which is mainly responsible for C. albicans MDR, has a promoter which is quite active in C. albicans and S. cerevisiae, even without the presence of additional transcription factor(s).

This promoter could not be used in the screening system of Kozowska et al. Moreover, also promoters of the transcription factors cannot be involved into the screening system as transcription factors can be introduced into the system only under the control of an inducible promoter. Otherwise, growth of the test strain is not possible. However, the upstream elements of a regulatory network are especially interesting as target for inhibition since they control the expression of several different MDR-genes. Consequently, such a screening system is not suitable to search for prospective agents to combat multidrug resistance in pathogenic organisms or cancerous cells.

Thus, there is a need for a test system which allows the identification of inhibitors of transcription of transporters which confer MDR and which furthermore allows the study of any element of the regulatory network controlling said transcription in said test system.

SUMMARY OF THE INVENTION

The present invention provides the first easy to handle and reliable high throughput system to identify substances that specifically inhibit target promoters or their transcription factors or even the promoters of the transcription factors. This system is able to identify specific inhibitors for the whole regulatory network of the expression of the target gene. In particular, the system enables the analysis of substances in an one-step high throughput procedure, based on an easily detectable positive growth phenotype.

This novel screening system is based on a facultative lethal reporter gene product. The gene product is only lethal for the cells under appropriate non-permissive conditions but under permissive conditions it does not hamper the cell growth. Therefore, test strains can be constructed under permissive conditions by transformation of a basal strain (expressing the reporter gene under the control of the particular target gene promoter) with corresponding transcription factor gene(s) including its/their promoter(s). The choice of potential target gene promoters is not limited, i.e., all promoters and their regulatory network, irrespective of their activity, can be included into the screening system. In this respect, the whole regulatory network that is present in the pathogenic/tumor cell is covered by the screen. Thus, the chance to find an inhibitor is significantly increased.

Moreover, the inhibition of the expression can occur at different steps in the regulatory network, e.g. at the promoter level of the transporter genes, at the level of transcription factor(s) of the promoters or even at the promoter level of the transcription factor(s). The inhibition of an upstream element of the regulatory network is more effective than inhibition of the promoter of the target gene since in the first case several drug pumps (all those under the control of the inhibited upstream regulatory element) would be inactivated concurrently. The present invention combines all advantages of the latest state of engineering: I) consideration of the whole regulatory network, II) exclusion of the detection of metabolic inhibitors, III) easy detection of specific effects in IV) a one-step-high-throughput system.

With this novel screening system substances can be found that hamper or undo the development of resistances by (re) sensitising formerly resistant cells. Contrary to new antibiotics and/or chemotherapeutics, to which cells develop resistance in due time, the novel inhibitors of the MDR-regulatory network to be screened cannot lead to development of extended resistance. Thus, the invention provides (1) a method for the identification of inhibitors of transcription factors and/or gene promoters (regulatory elements) within a transcriptional regulatory network by a positive phenotype using a genetically modified yeast strain (test yeast strain) which is transformed with a functional nucleic acid segment comprising
(a) a gene encoding a facultatively lethal reporter protein; and
(b) a promoter controlling the expression of said gene (a);
(2) a preferred embodiment of the method of (1) above, wherein the promoter (b) in the test yeast strain is a part of the transcriptional regulatory network;
(3) a modified yeast strain which is transformed with a functional nucleic acid segment comprising
(a) a gene encoding a facultatively lethal reporter protein; and
(b) a promoter controlling the expression of said gene (a);
(4) a preferred embodiment of the modified yeast strain as defined in (3) above,
wherein the promoter (b) is a part of a regulatory network and optionally the yeast strain further comprises
(c) one or more additional gene(s) encoding a component of the regulatory network of said promoter, preferably encoding one or more transcription factor(s) controlling said promoter, and wherein said additional gene(s) is/are preferably comprised in the functional nucleic acid segment as defined in (3) above;
(5) a preferred embodiment of the modified yeast strain defined in (3) or (4) above, wherein
(i) the yeast strain is a mutant strain lacking genes coding for transporters, preferably hexose transporters, more preferably glucose transporters, and preferably a S. cerevisiae mutant strain, most preferably the S. cerevisiae mutant RE700A (MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3); and/or
(ii) the gene encoding the facultatively lethal reporter protein is a gene encoding a protein which under certain culture conditions gives rise to a lethal phenotype (reporter gene), preferably said reporter gene is selected from genes encoding membrane integral proteins including transporter genes such as HXT1-7 and Ght1-6, most preferably said transporter gene is S. cerevisiae HXT7; and/or
(iii) the promoter is selected from yeast promoters and promoters controlling the expression of MDR conferring genes, preferably from S. cerevisiae promoters (preferably promoters of the PDR gene family, most preferably the S. cerevisiae PDR5-promoter ($P_{PDR5}$)), human pathogenic yeast promoters (preferably from Candida spp., most preferably from C. albicans, especially the C. albicans CDR1-promoter $P_{CDR1}$ and the C. albicans CDR2-promoter $P_{CDR2}$), promoters controlling the expression of MDR conferring genes in pathogens or mammalian tumor cells, and constitutively active yeast promoters (preferably the yeast PMA1-promoter (PPMA1));
(6) the modified yeast strain as defined in (3) to (5) above which is S. cerevisiae RE700A i $P_{PDR5}$-HXT7 (MATa ura3-52 his3-11,15 lue2-3,112 MAL2 SUC2 GAL MEL hxt1Δ::

HIS3::Δhxt4 hxt5:: LEU2 hxt2Δ:: HIS3 hxt3Δ:: LEU2::Δhxt6 hxt7:: HIS3 tok1::P$_{PDR5}$HXT7) deposited as DSM 16852;

(7) an integration vector comprising a functional nucleic acid segment as defined in (3) to (6) above;

(8) a method for the preparation of a modified yeast strain as defined in (3) to (6) above, comprising the integration of said functional nucleic acid segment into a yeast host strain using an integration vector as defined in (7) above;

(9) the use of a yeast strain as defined in (3) to (6) above for testing the inhibition of the promoters and/or transcription factors involved in regulatory networks, especially in MDR (Multiple Drug Resistance) of pathogens or tumor cells; and

(10) a kit for performing the method as defined in (1) or (2) above, comprising a modified yeast strain as defined (3) to (6) above and/or an integration vector as defined in (7) above.

BRIEF DESCRIPTION OF THE FIGURES

The following figures are provided in order to further explain further the invention.

(A) RE700A, ECFP and ET[PDR] were incubated 20 h at 28° C. with maltose (2% (w/v)) as the sole carbon source in the presence of the indicated 2-DG concentrations. The optical density was measured at 600 nm every 15 minutes and the integral under the growth curve was calculated. Inhibition of growth of ECFP and ET[PDR] is shown in percent of growth of RE700A. Growth of ECFP was inhibited by 39% at 0.005% (w/v) 2-DG, by 78% at 0.01% (w/v) 2-DG, by 91% at 0.03% (w/v) 2-DG and by 93% at 0.05% (w/v) 2-DG. Growth of ET[PDR] was inhibited by 52% at 0.005% (w/v) 2-DG, by 87% at 0.01% (w/v) 2-DG, by 94% at 0.03% (w/v) 2-DG and by 96% at 0.05% (w/v) 2-DG.

(B) RE700A, ICFP and IT[PDR] were incubated 20 h at 28° C. with maltose (2% (w/v)) as the sole carbon source and the indicated 2-DG concentrations. The optical density was measured at 600 nm every 15 minutes and the integral under the growth curve is calculated. Inhibition of growth of ICFP and IT[PDR] is shown in percent of growth of RE700A. Growth of ICFP was inhibited by 15% at 0.01% (w/v) 2-DG, by 74% at 0.03% (w/v) 2-DG, by 80% at 0.05% (w/v) 2-DG and by 83% at 0.1% (w/v) 2-DG. Growth of IT[PDR] was inhibited by 21% at 0.01% (w/v) 2-DG, by 79% at 0.03% (w/v) 2-DG, by 88% at 0.05% (w/v) 2-DG and by 96% in 0.1% (w/v) 2-DG.

FIG. 4:

(A) Growth inhibition of RE700A i P$_{PDR5}$-HXT7 (IT[PDR]), RE700A Δpdr1 tok1::P$_{PDR5}$-HXT7, RE700A Δpdr3 tok1::P$_{PDR5}$-HXT7 and RE700A Δpdr1,pdr3 tok1::P$_{PDR5}$-HXT7 at increasing 2-DG concentrations. RE700A i P$_{PDR5}$-HXT7 (IT[PDR]), RE700A Δpdr1 tok1::P$_{PDR5}$-HXT7, RE700A Δpdr3 tok1::P$_{PDR5}$-HXT7 and RE700A Δpdr1,pdr3 tok1::P$_{PDR5}$-HXT7 were incubated 20 h at 28° C. with Maltose (2% (w/v)) as the sole carbon source and 2-DG concentrations as indicated. The optical density was measured at 600 nm every 15 minutes and the integral under the growth curve was calculated. Inhibition of growth caused by 2-DG is shown in percent. The growth of the strain RE700A tok1::P$_{PDR5}$-HXT7 (IT[PDR]) was inhibited by 50% at 0.02% (w/v) 2-DG. Growth of the strains RE700A Δpdr1 tok1::P$_{PDR5}$-HXT7 and RE700A Δpdr3 tok1::P$_{PDR5}$-HXT7 was inhibited by 50% at 0.026% (w/v) 2-DG. The growth of the strain RE700A Δpdr1,pdr3 tok1::P$_{PDR5}$-HXT7 was not significantly inhibited up to a 2-DG concentration of 0.03% (w/v).

(B) Relative growth of RE700A tok1::P$_{PDR5long}$-HXT7, RE700A Δpdr1 tok1::P$_{PDR5long}$-HXT7, RE700A Δpdr3 tok1::P$_{PDR5long}$-HXT7 and RE700A Δpdr1,3 tok1::P$_{PDR5long}$-HXT7 in the presence of 2-DG. Cells were incubated for 20 h at 28° C. with 2-DG at different concentrations. RE700A Δpdr1,3 tok1::P$_{PDR5long}$-HXT7 cells were far less sensitive to 2-DG compared with RE700A Δpdr1 tok1::P$_{PDR5long}$-HXT7, RE700A Δpdr3 tok1::P$_{PDR5long}$-HXT7 and especially RE700A tok1::P$_{PDR5long}$-HXT7 cells. The standard error of the mean (n=5) is indicated.

Figure 5:
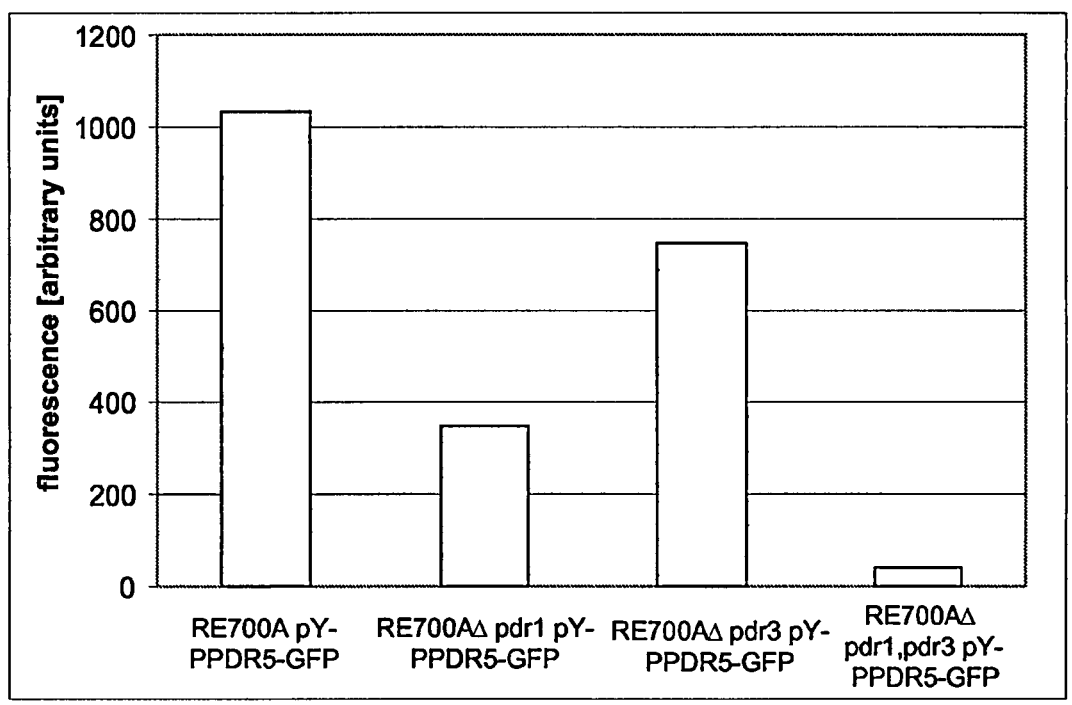

FIG. 5: GFP fluorescence measurements of the strains RE700A [pY-PPDR5-GFP], RE700A ?pdr1 [pY-PPDR5-GFP], RE700A ?pdr3 [pY-PPDR5-GFP] and RE700A ?pdr1,pdr3 [pY-PPDR5-GFP] after 12 h incubation at 28° C. Fluorescence measurement of the strain RE700A [pY-P$_{PDR5}$-GFP] after 12 h incubation displayed a fluorescence of 1000 arbitrary units. Fluorescence measurement of the strain RE700A Δpdr1 [pY-P$_{PDR5}$-GFP] displayed a decreased fluorescence of 350 arbitrary units. Fluorescence measurement of the strain RE700A Δpdr3 [pY-P$_{PDR5}$-GFP] displayed a fluorescence of 750 arbitrary units, and fluorescent measurement of the strain RE700A Δpdr1, pdr3 [pY-P$_{PDR5}$-GFP] displayed a fluorescence of only 43 arbitrary units.

Figure 6:
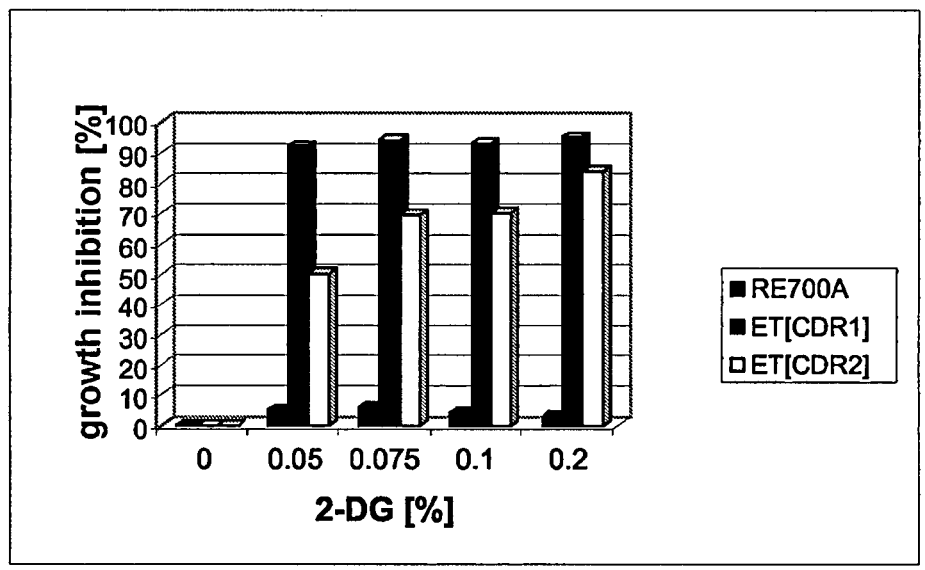

FIG. 6: Growth inhibition of RE700A, ET[CDR1] and ET[CDR2] in the presence of increasing 2-DG concentrations after 20 h incubation at 28° C. for in liquid medium. RE700A, ET[CDR1] and ET[CDR2] were incubated 20 h at 28° C. with maltose (2% (w/v)) as the sole carbon source in the presence of increasing 2-DG concentrations in liquid medium. The optical density was measured at 600 nm semi-continuously every 15 minutes and the integral under the growth curve was calculated. Inhibition of growth is shown in percent compared to growth in the absence of 2-DG. Growth of ET[CDR1] was inhibited by 92% at a 2-DG concentration in liquid media of 0.05% (w/v), by 94% at a 2-DG concentration in liquid media of 0.075% (w/v), by 93% at a 2-DG concentration in liquid media of 0.1% (w/v) and by 95% at a 2-DG concentration of 0.2% (w/v). Growth of ET[CDR2] was inhibited by 50% at a 2-DG concentration in liquid media of 0.05% (w/v), by 70% at a 2-DG concentration in liquid media of 0.075% (w/v), by 70% at a 2-DG concentration in liquid media of 0.1% (w/v) and by 84% at a 2-DG concentration of 0.2% (w/v).

Figure 7:
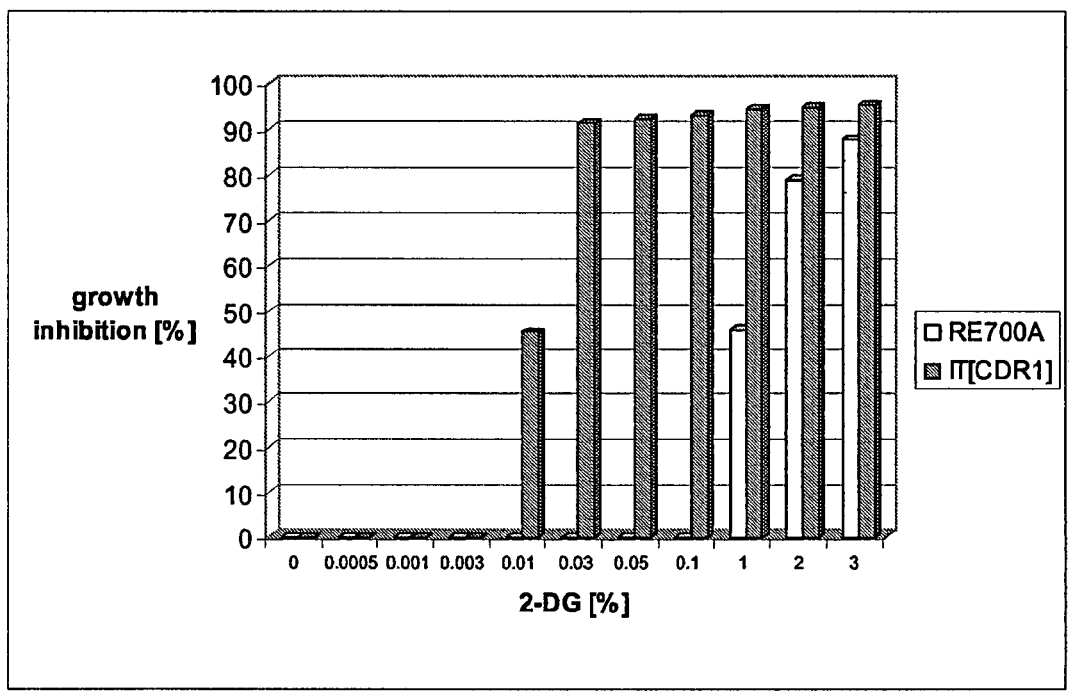

FIG. 7: Growth inhibition of RE700A and IT[CDR1] by 2-DG. RE700A and IT[CDR1] were incubated for 20 h at 28° C. with maltose (2% (w/v)) as the sole carbon source and increasing 2-DG concentrations as indicated. The optical density was measured at 600 nm every 15 minutes and the integral under the growth curve was calculated. Inhibition of growth is shown in percent regarding growth in the absence of 2-DG. Growth of IT[CDR1] was inhibited by 45% at a 2-DG concentration of 0.01% (w/v), by 91% at a 2-DG concentration of 0.03% (w/v), by 92% at a 2-DG concentration of 0.05% (w/v), by 92% at a 2-DG concentration of 0.1% (w/v), by 94% at a 2-DG concentration of 1% (w/v), by 95% at a 2-DG concentration of 2% (w/v) and by 95% at a 2-DG concentration of 3% (w/v).

Figure 8:
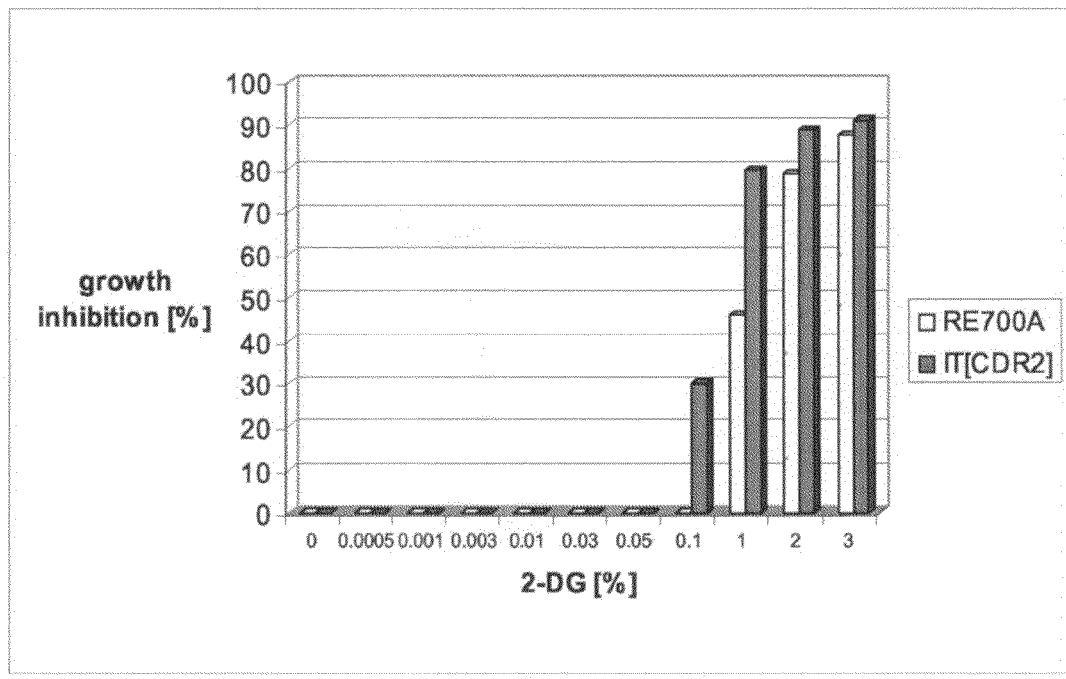

FIG. 8: Growth inhibition of RE700A and IT[CDR2] by 2-DG. RE700A and IT[CDR2] were incubated for 20 h at 28° C. with maltose (2% (w/v)) as the sole carbon source and increasing 2-DG concentrations as indicated. The optical density was measured at 600 nm every 15 minutes and the integral under the growth curve was calculated. Inhibition of growth is shown in percent regarding growth in the absence of 2-DG. Growth of IT[CDR2] was inhibited by 30% at a 2-DG concentration of 0.1% (w/v), by 79% at a 2-DG concentration of 1% (w/v), by 89% at a 2-DG concentration of 2% (w/v), by 91% at a 2-DG concentration of 3% (w/v).

Figure 9A:
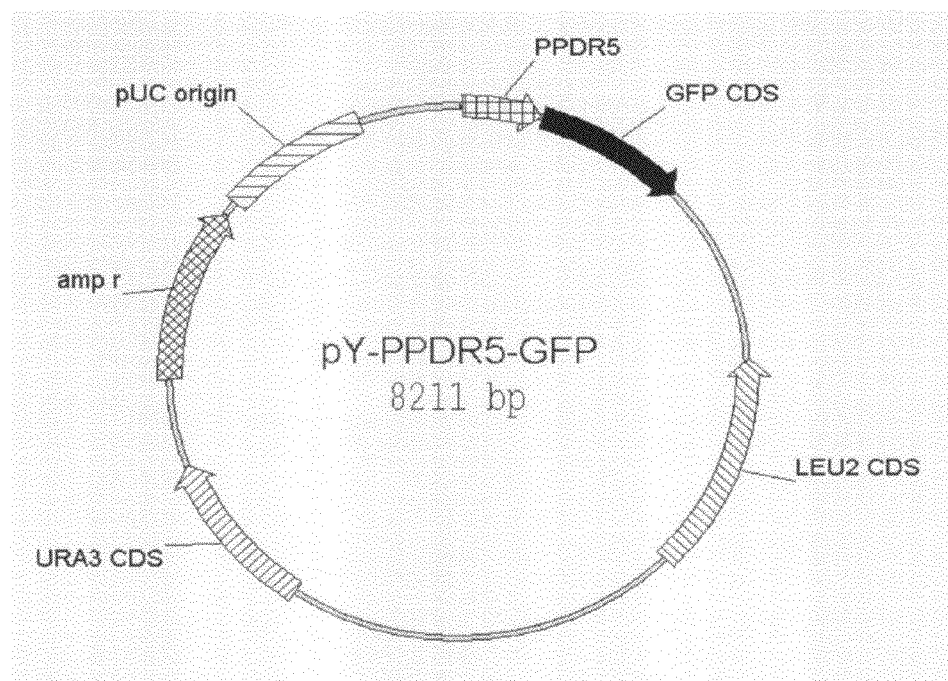
Figure 9B:
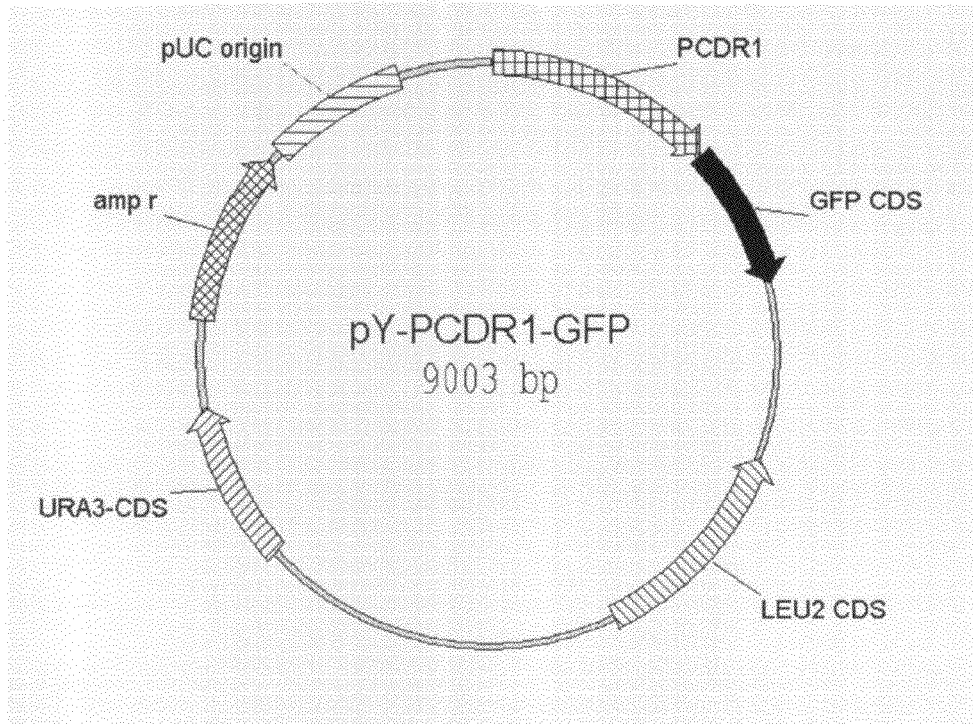
Figure 9C:
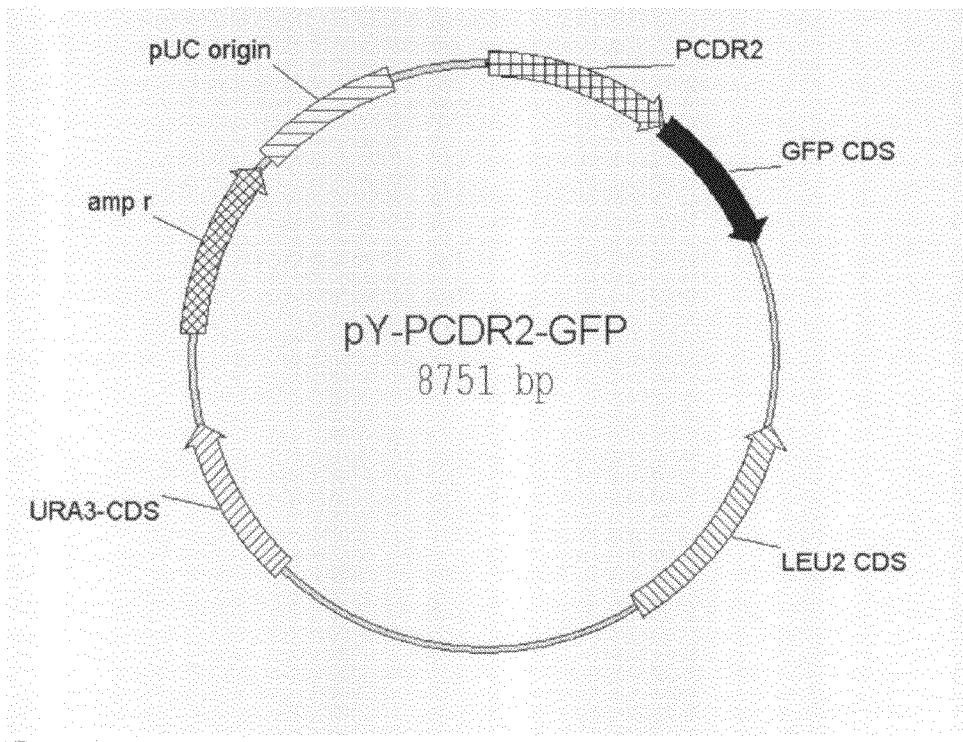
Figure 10A:
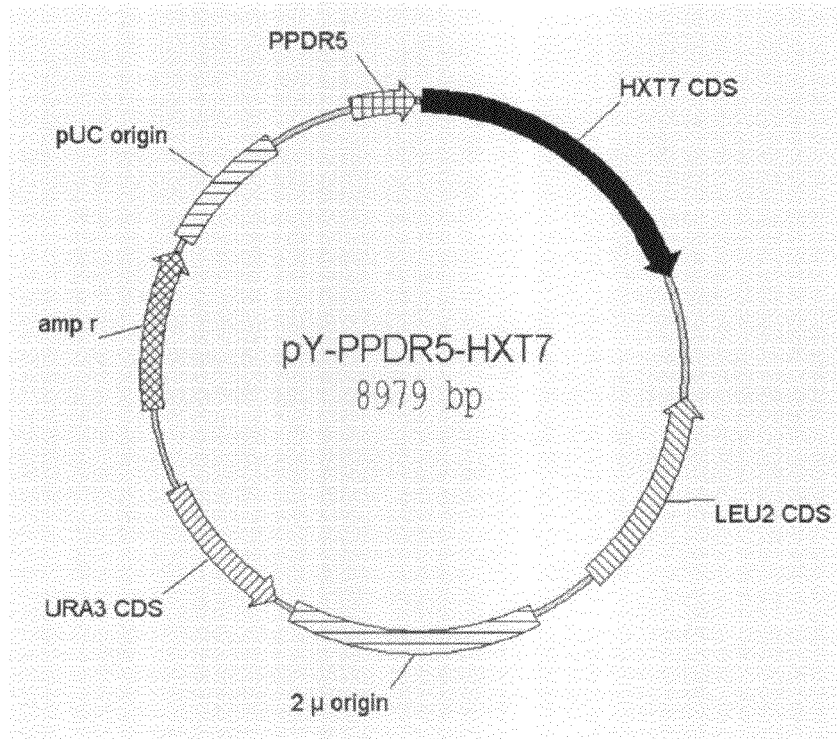
Figure 10B:
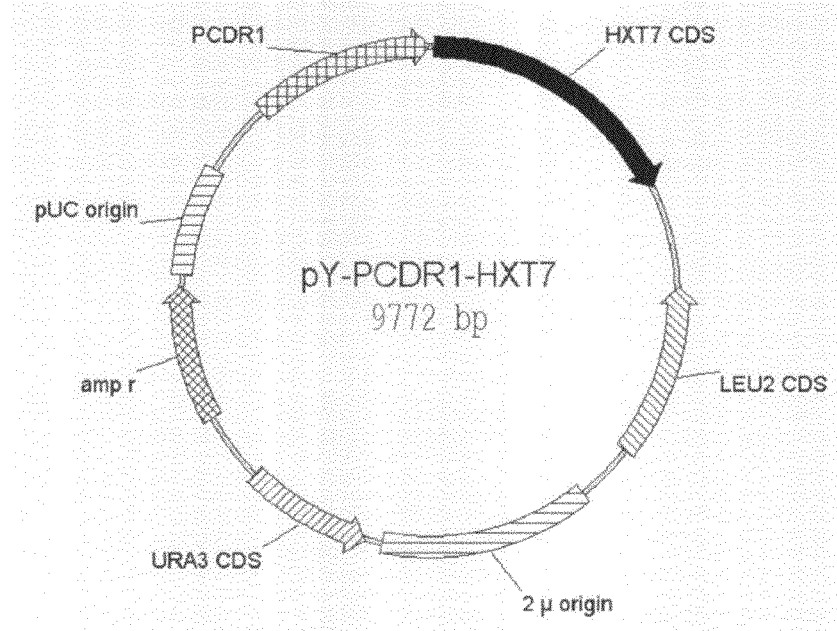
Figure 10C:
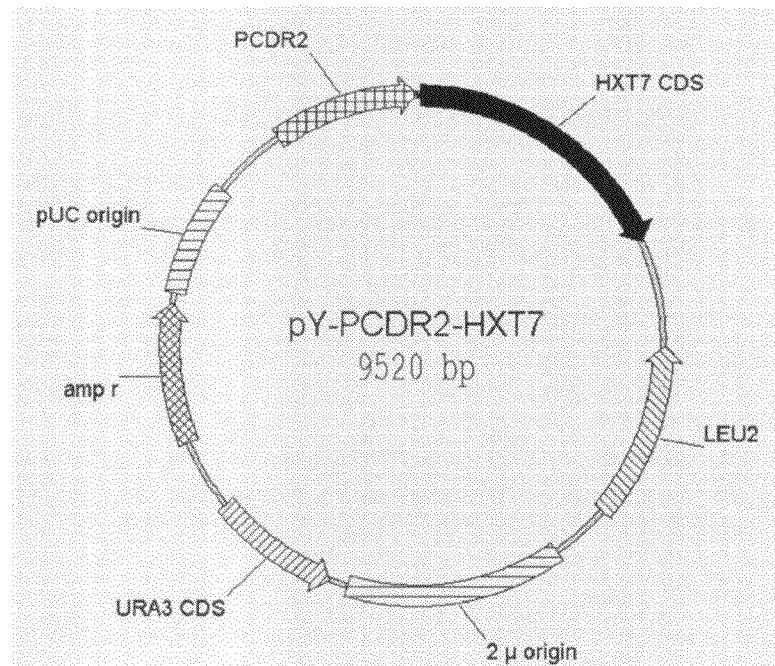
Figure 10D:
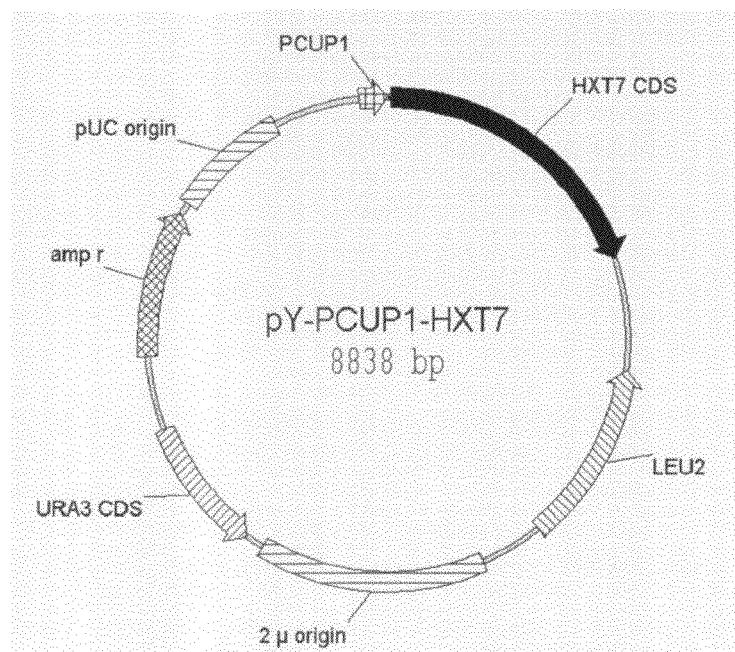

FIG. 9: Schematic maps of shuttle plasmids pY-PPDR5-GFP (A; SEQ ID NO:34), pY-PCDR1-GFP (B; SEQ ID NO:38) and pY-PCDR2-GFP (C; SEQ ID NO:40). In yeast the URA3 gene is used as auxotrophic marker, in bacteria expression of the β lactamase gene (ampr) mediates ampicillin resistance. The reporter gene HXT7 is expressed under the control of PPDR5 (A), PCDR1 (B) and PCDR2 (C).

FIG. 10: Schematic maps of shuttle plasmids pY-PPDR5-HXT7 (A; SEQ ID NO:36), pY-PCDR1-HXT7 (B; SEQ ID NO:37), pY-PCDR2-HXT7 (C; SEQ ID NO:39) and pY-$P_{CUP1}$-HXT7 (D; SEQ ID NO:41). In yeast the URA3 gene is used as auxotrophic marker, in bacteria expression of the β-lactamase gene (ampr) mediates ampicillin resistance. The reporter gene HXT7 is expressed under the control of PPDR5 (A), PCDR1 (B), PCDR2 (C) and PCUP1 (D).

Figure 11A:
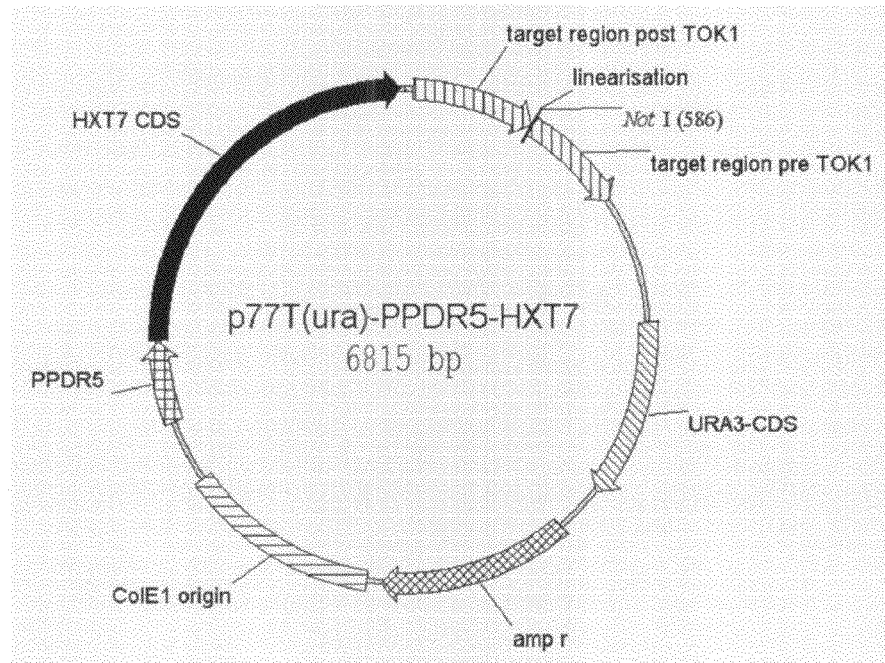
Figure 11B:
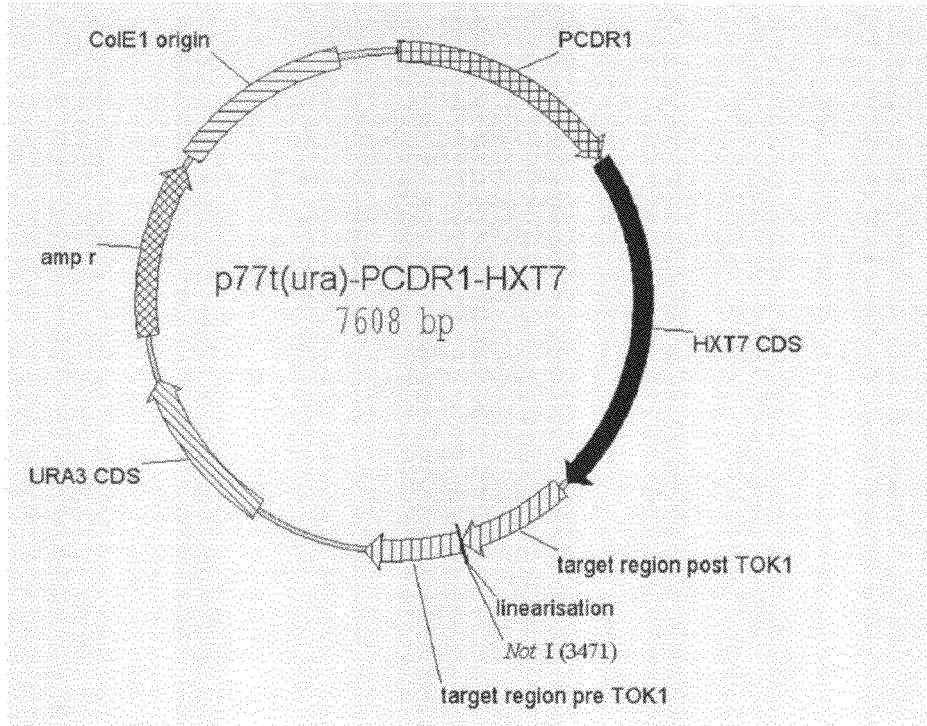
Figure 11C:
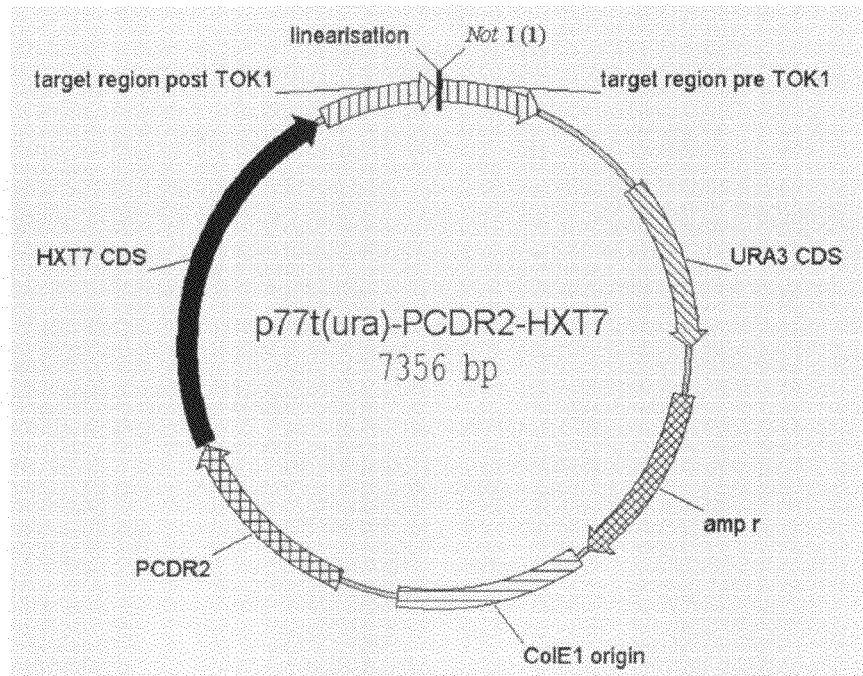
Figure 11D:
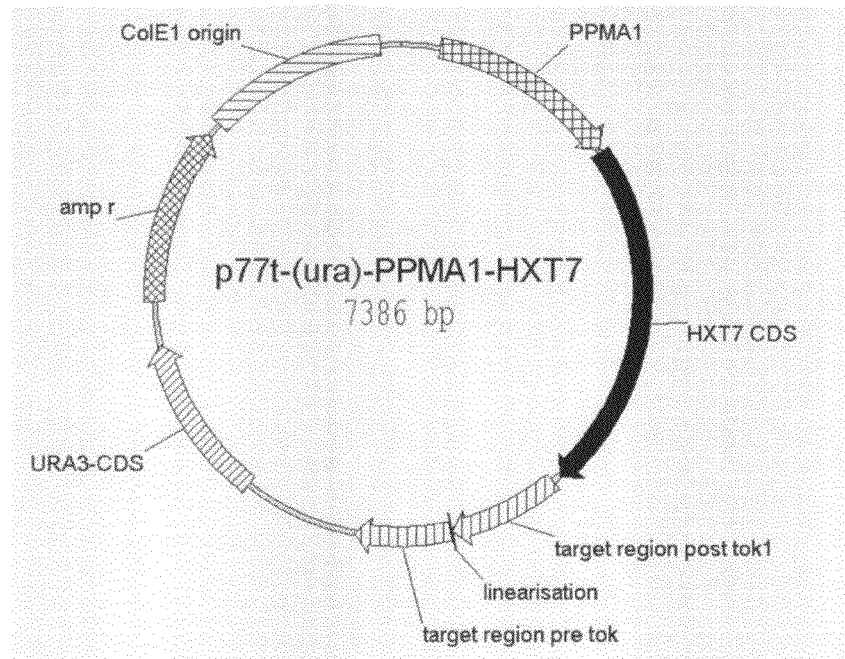
Figure 11:
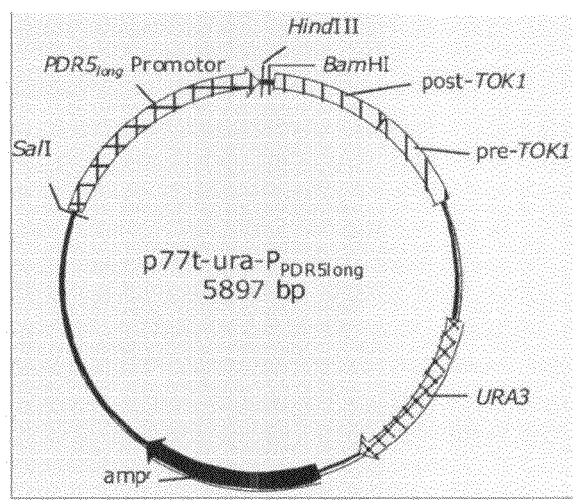

FIG. 11: Schematic maps of TOK1-integration plasmids p77t-(ura)-$P_{PDR5}$-HXT7 (A; SEQ ID NO:48), p77t-(ura)-$P_{CDR1}$-HXT7 (B; SEQ ID NO:49), p77t-(ura)-$P_{CDR2}$-HXT7 (C; SEQ ID NO:50) and p77t-(ura)-$P_{PMA1}$-HXT7 (D; SEQ ID NO:51). In yeast the URA3 gene is used as auxotrophic marker, in bacteria expression of the β-lactamase gene (amp$^r$) mediates ampicillin resistance. To enable/facilitate integration into the S. cerevisiae TOK1 locus plasmids were linearised by digestion with NotI located between the target regions post TOK1 and pre TOK1. The reporter gene HXT7 is expressed under the control of $P_{PDR5}$ (A), $P_{CDR1}$ (B), $P_{CDR2}$ (C) and $P_{PDR5long}$ (E).

Figure 12A:
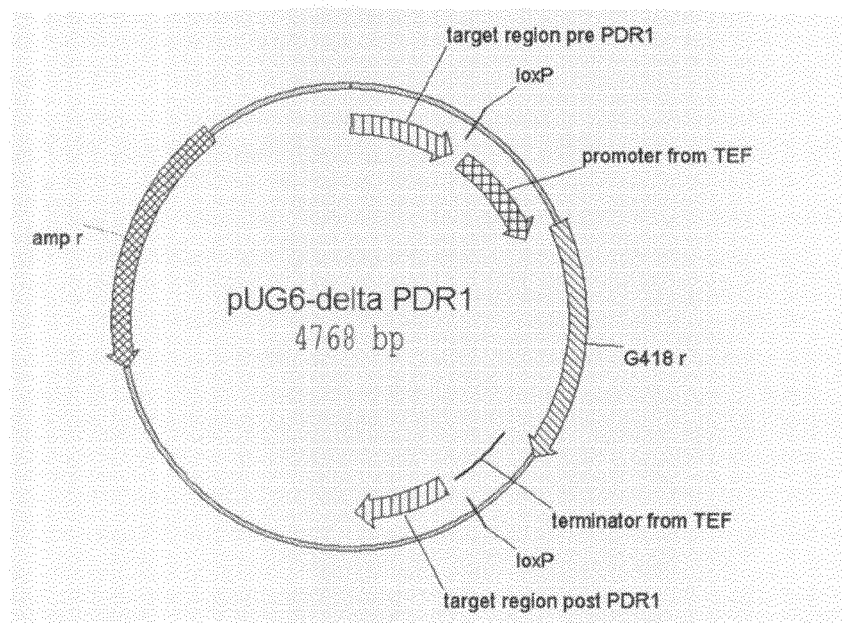
Figure 12B:
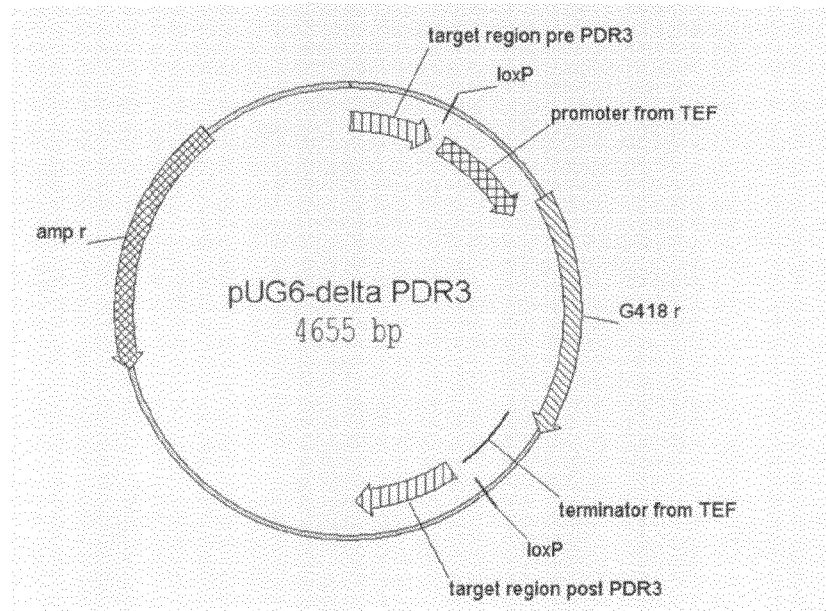

FIG. 12: Schematic maps of the plasmids pUG6-Δpdr1 (A) (SEQ ID NO:53) and pUG6-Δpdr3 (B) (SEQ ID NO:56) carrying deletion cassettes for the S. cerevisiae genes PDR1 and PDR3, respectively. Both plasmids are based on puG6 (Güldener, U. et al, Nucleic Acids Research 24:2519-2524 (1996)). They contain deletion cassettes for PDR1 and PDR3, respectively, consisting of up- and downstream targeting regions (pre PDR1, pre PDR3, post PDR1 and post PDR3, respectively) flanking a G418 cassette (promoter from TEF, G418 r and the terminator from TEF). The additional presence of loxP sites flanking the G418-cassette allows removal of this cassette from generated strains.

Figure 13:
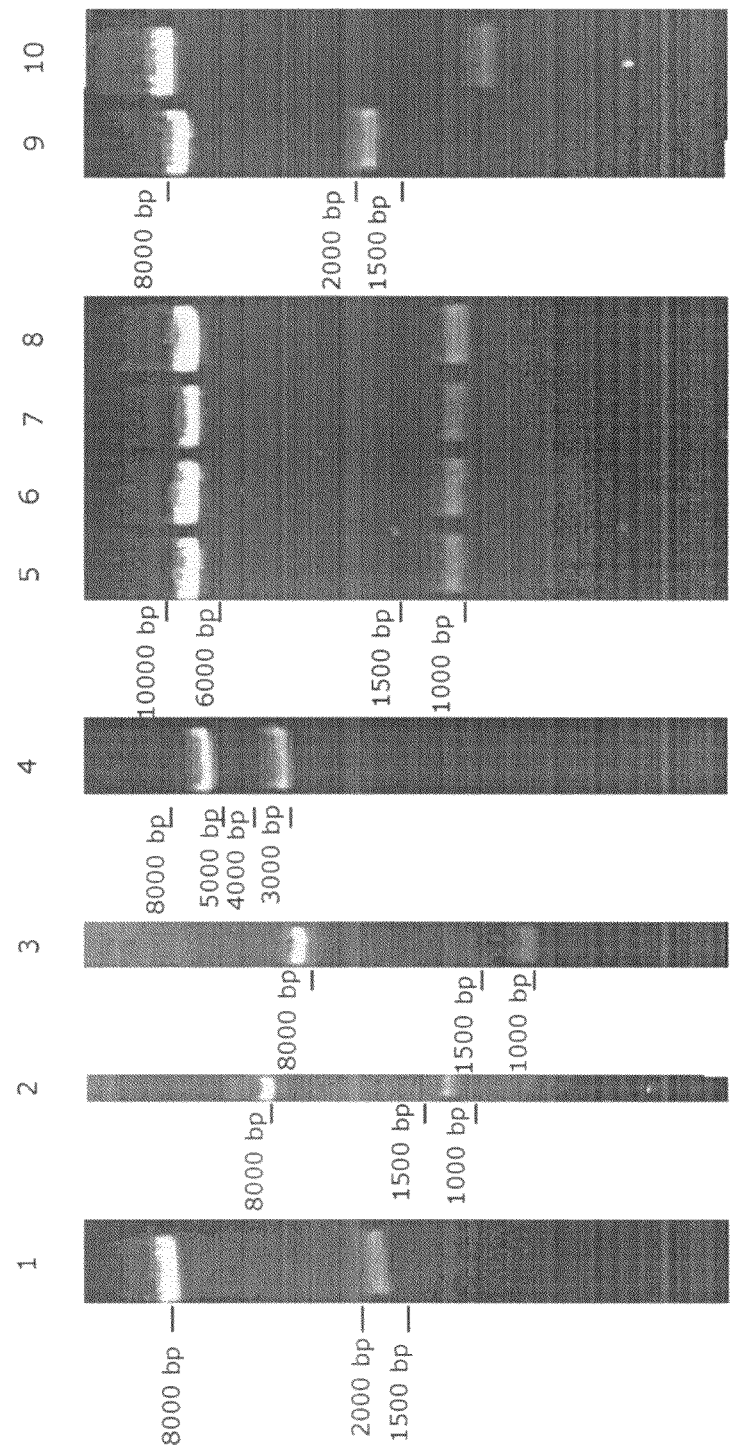

FIG. 13: Agarose gel electrophoresis of plasmid DNA digested with the restriction enzymes detailed below to analyse authenticity of plasmids in transformed yeast strains. The plasmids were recovered from transformed S. cerevisiae RE700A, RE700A Δpdr1, RE700A Δpdr3, and RE700A Δpdr1, pdr3 strains and analysed with restriction enzymes. Lanes: 1, 7.251 kb and 1.728 kb BamHI/EcoRI fragments of plasmid pY-$P_{PDR5}$-HXT7 recovered from ET[PDR]; 2, 8.440 kb and 1.332 kb HindIII fragments of plasmid pY-$P_{CDR1}$-HXT7 recovered from ET[CDR1]; 3, 8.440 kb and 1.080 kb HindIII fragments of plasmid pY-$P_{CDR2}$-HXT7 recovered from ET[CDR2]; 4, 5.643 kb and 3.195 kb EcoRV fragments of plasmid pY-$P_{CUP1}$-HXT7 recovered from ECFP; 5, 7.074 kb and 1.137 kb HindIII fragments of plasmid pY-$P_{PDR5}$-GFP recovered from CQ[PDR]; 6, 7.074 kb and 1.137 kb HindIII fragments of plasmid pY-$P_{PDR5}$-GFP recovered from RE700A Δpdr1 [pY-$P_{PDR5}$-GFP]; 7, 7.074 kb and 1.137 kb HindIII fragments of plasmid pY-$P_{PDR5}$-GFP recovered from RE700A Δpdr3 [pY-$P_{PDR5}$-GFP]; 8, 7.074 kb and 1.137 kb HindIII fragments of plasmid pY-$P_{PDR5}$-GFP recovered from RE700A Δpdr1, pdr3 [pY-$P_{PDR5}$-GFP]; 9, 7.074 kb and 1.929 kb HindIII fragments of plasmid pY-$P_{CDR1}$-GFP recovered from CQ[CDR1]; 10, 7.793 kb and 0.958 kb BamHI/EcoRI fragments of plasmid pY-$P_{CDR2}$-GFP recovered from CQ[CDR2]. The restriction analysis verified RE700A e $P_{PDR5}$-HXT7 (ET[PDR]), RE700A e $P_{CDR1}$-HXT7 (ET [CDR1]), RE700A e $P_{CDR2}$-HXT7 (ET[CDR2]), RE700A e $P_{PDR5}$-GFP (CQ[PDR]), RE700A e $P_{CDR1}$-GFP (CQ [CDR1]), RE700A e $P_{CDR2}$-GFP (CQ[CDR2]), RE700A e $P_{CUP1}$-HXT7 (ECFP), RE700A Δpdr1 [pY-$P_{PDR5}$-HXT7], RE700A Δpdr3 [pY-$P_{PDR5}$-HXT7], RE700A Δpdr1,pdr3 [pY-$P_{PDR5}$-HXT7].

Figure 14:
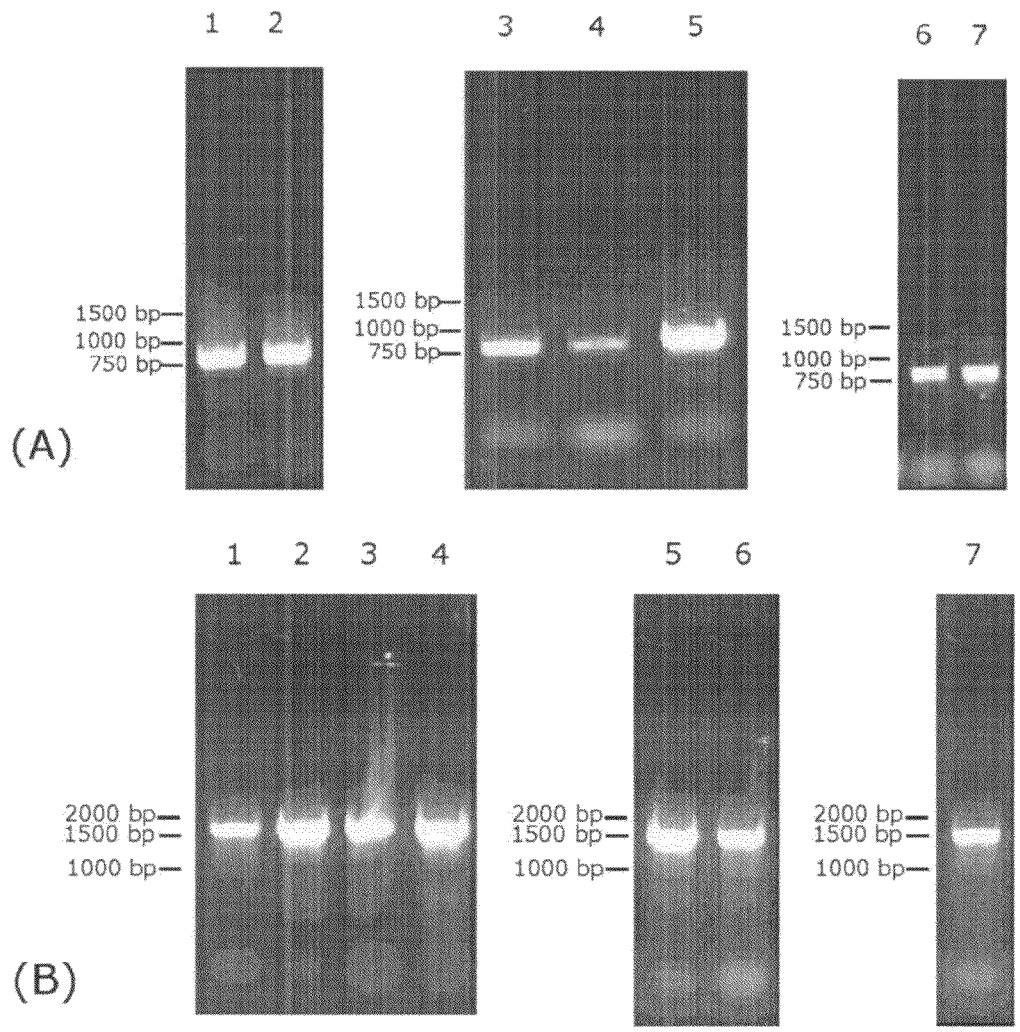

FIG. 14: Verification of correct integration of replacement cassettes into the tok1 locus by diagnostic PCR analysis. The correct integration of the replacement cassettes (p77t-(ura)-$P_{PDR5}$-HXT7, p77t-(ura)-$P_{CDR1}$-HXT7, p77t-(ura)-$P_{CDR2}$-HXT7 and p77t-(ura)-$P_{PMA1}$-HXT7) into the tok1 locus were verified by diagnostic PCR using cassette-internal and external primers. (A) For 5' integration verification primers (SEQ ID NO:62, 63) were used in PCR to amplify a DNA fragment of 770 bp with genomic DNA of below indicated strains as template. (B) For 3' integration verification primers (SEQ ID NO:64, 65) were used in PCR to amplify a DNA fragment of 1402 bp with genomic DNA of below indicated strains as template. The analysis proofed the authenticity of RE700A i $P_{PDR5}$-HXT7 (IT[PDR]) (lane1), RE700A $P_{CDR1}$-HXT7 (IT [CDR1]) (lane2), RE700A i $P_{CDR2}$-HXT7 (IT[CDR2]) (lane3), RE700A $P_{PMA1}$-HXT7 (ICFP) (lane4), RE700A ?pdr1 tok1::$P_{PDR5}$-HXT7 (lane5), RE700A ?pdr3 tok1:: $P_{PDR5}$-HXT7 (lane6) and RE700A ?pdr1,pdr3 tok1::$P_{PDR5}$-HXT7 (lane7) (table 1).

Figure 15:
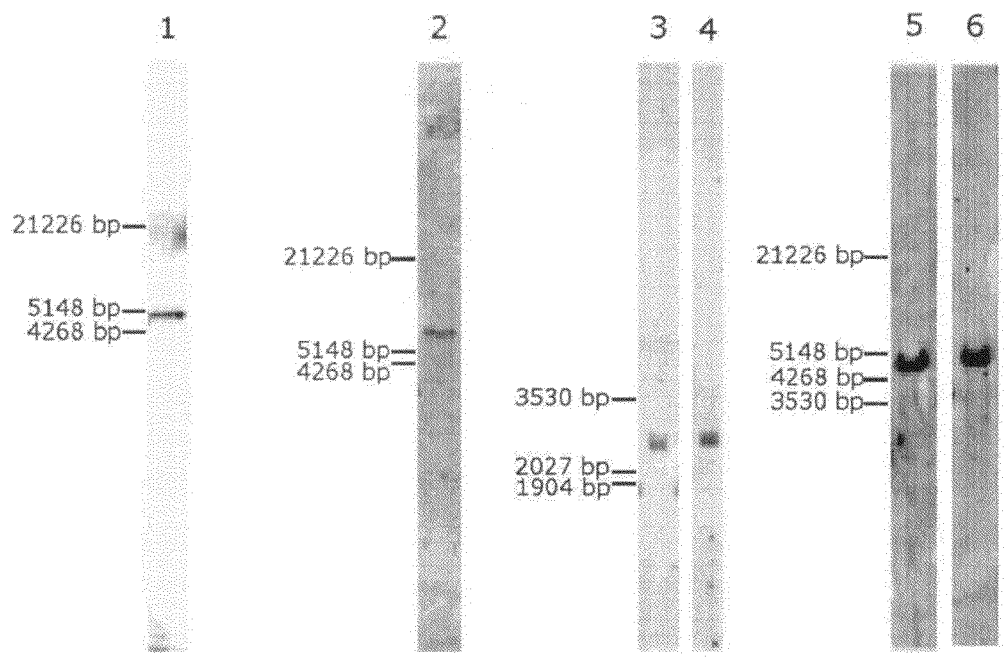

FIG. 15: Southern blot analysis of pdr1 and pdr3 deletion mutant strains. 1: RE700A ?pdr1 cut with ("c") PstI and hybridised with ("h") pre-pdr1 (SEQ ID NO:66); 2: RE700A ?pdr1 c BglII h post-pdr1 (SEQ ID NO:67); 3: RE700A ?pdr3 c PstI h pre-pdr3 (SEQ ID NO:72); 4: RE700A ?pdr1,pdr3 c PstI h pre-pdr3; 5: RE700A ?pdr3 c BglII h post-pdr3 (SEQ ID NO:73); 6: RE700A ?pdr1,pdr3 c BglII h post-pdr3. Expected lengths of labelled fragments were: 5.045 kb for DNA from pdr1 deleted strains digested with PstI and probed with pre-pdr1; 7.821 kb for DNA from pdr1 deleted strains digested with BglII and probed with post-pdr1 (SEQ ID NO:67); 3.394 kb for DNA from pdr3 deleted strains digested with PstI and probed with pre-pdr3 (SEQ ID NO: 72) and 4.842 kb for DNA from pdr3 deleted strains digested with BglII and probed with post-pdr3 (SEQ ID NO:73). The signals obtained (lane1-6) corresponded well to this values and thus proved the authenticity of the strains RE700A ?pdr1, RE700A ?pdr3 and RE700A ?pdr1,pdr3 (Table 1). Since the double deletion strain RE700A ?pdr1,pdr3 was generated from RE700A ?pdr1, the pdr1 locus was not re-analysed in the RE700A ?pdr1,pdr3.

Figure 16:
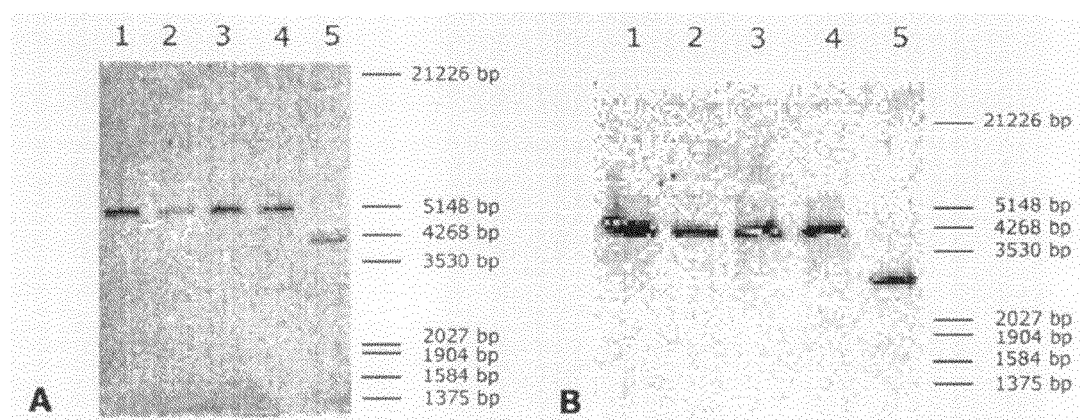

FIG. 16: Southern blot analysis of $P_{PDR5long}$-HXT7 integration into the TOK1 locus of S. cerevisiae.

(A) Genomic DNA was cut with PstI and hybridised with dixoxigenin-labeled pre-tok-fragments (SEQ ID NO: 86). The DNA was isolated from 1: RE700A tok1::$P_{PDR5long}$-

HXT7, 2: RE700A ?pdr1 tok1::P$_{PDR5long}$-HXT7, 3: RE700A ?pdr3 tok1::P$_{PDR5long}$-HXT7, 4: RE700A ?pdr,3 tok1::P$_{PDR5long}$-HXT7, 5: RE700A.

(B) Genomic DNA was cut with EcoRV and hybridised with dixoxigenin-labeled post-tok-fragments (SEQ ID NO: 87). The DNA was isolated from 1: RE700A tok1::P$_{PDR5long}$-HXT7, 2: RE700A ?pdr1 tok::P$_{PDR5long}$-HXT7, 3: RE700A ?pdr3 tok1::P$_{PDR5long}$-HXT7, 4: RE700A ?pdr1,3 tok1::P$_{PDR5long}$-HXT7, 5: RE700A. The signals obtained corresponded well to the expected values (Tab. 4) and proved the authenticity of the said strains.

Sequence Listing - Free Text

| SEQ ID NO: | Description |
|---|---|
| 1 | PCR-HXT7 |
| 2 | primer HXT7_sense |
| 3 | primer HXT7_antisense |
| 4 | PCR-P$_{PDR5}$ |
| 5 | primer P$_{PDR5}$_sense |
| 6 | PDR5 (NCBI geneID: 854324, NC_001147, S. cerevisiae chromosome XV, 619840-624375) |
| 7 | primer P$_{PDR5}$_antisense |
| 8 | PCR-pre-PDR1 |
| 9 | primer pre_PDR1_sense |
| 10 | PDR1 |
| 11 | primer pre_PDR1_antisense |
| 12 | PCR-post-PDR1 |
| 13 | primer post_PDR1_sense |
| 14 | primer post_PDR1_antisense |
| 15 | PCR-pre-PDR3 |
| 16 | primer pre_PDR3_sense |
| 17 | PDR3 |
| 18 | primer pre_PDR3_antisense |
| 19 | PCR-post-PDR3 |
| 20 | primer post_PDR3_sense |
| 21 | primer post_PDR3_antisense |
| 22 | pYEX ™-BX |
| 23 | PCR-URA3 |
| 24 | primer ura3_sense |
| 25 | primer ura3_antisense |
| 26 | PCR-P$_{CDR1}$ |
| 27 | primer P$_{CDR1}$_sense |
| 28 | CDR1 |
| 29 | primer P$_{CDR1}$_antisense |
| 30 | PCR-P$_{CDR2}$ |
| 31 | primer P$_{CDR2}$_sense |
| 32 | CDR2 |
| 33 | primer P$_{CDR2}$_antisense |
| 34 | pY-P$_{PDR5}$-GFP |
| 35 | pYEX-BX-rad54/GFP |
| 36 | pY-P$_{PDR5}$-HXT7 |
| 37 | pY-P$_{CDR1}$-HXT7 |
| 38 | pY-P$_{CDR1}$-GFP |
| 39 | pY-P$_{CDR2}$-HXT7 |
| 40 | pY-P$_{CDR2}$-GFP |
| 41 | pY-P$_{CUP1}$-HXT7 |
| 42 | pYEX-BX-GFP |
| 43 | TOK1 |
| 44 | p77x |
| 45 | p77t-(ura) |
| 46 | p77t-w/o-prom |
| 47 | p77t-(ura)-w/o-prom |
| 48 | p77t-(ura)-P$_{PDR5}$-HXT7 |
| 49 | p77t-(ura)-P$_{CDR1}$-HXT7 |
| 50 | p77t-(ura)-P$_{CDR2}$-HXT7 |
| 51 | p77t-(ura)-P$_{PMA1}$-HXT7 |
| 52 | pYEX-P$_{PMA1}$-HXT7 |
| 53 | pUG6-Δpdr1 |
| 54 | pUG6 |
| 55 | pUG6-pre-pdr1 |
| 56 | pUG6-Δpdr3 |
| 57 | pUG6-pre-pdr3 |
| 58 | primer Δpdr1_sense |
| 59 | primer Δpdr1_antisense |
| 60 | primer Δpdr3_sense |
| 61 | primer Δpdr3_antisense |
| 62 | primer int_pre_tok_sense |
| 63 | primer int_pre_tok_antisense |
| 64 | primer int_post_tok_sense |
| 65 | primer int_post_tok_antisense |
| 66 | hybridisation probe pre-pdr1 |
| 67 | hybridisation probe post-pdr1 |
| 68 | primer hyb_pre_pdr1_sense |
| 69 | primer hyb_pre_pdr1_antisense |
| 70 | primer hyb_post_pdr1_sense |
| 71 | primer hyb_post_pdr1_antisense |
| 72 | hybridisation probe pre-pdr3 |
| 73 | hybridisation probe pst-pdr3 |
| 74 | primer hyb_pre_pdr3_sense |
| 75 | primer hyb_pre_pdr3_antisense |
| 76 | primer hyb_post_pdr3_sense |
| 77 | primer hyb_post_pdr3_antisense |
| 78 | pY-P$_{PMA1}$-GFP |
| 79 | pUC18-PMA1 |
| 80 | primer PPMA1_sense |
| 81 | primer PPMA1_antisense |
| 82 | pUC18 |
| 83 | PMA1 |
| 84 | p77t-(ura)-P$_{PDR5long}$-HXT7 |
| 85 | pSK-P$_{PDR5}$-PPUS |
| 86 | pre TOK |
| 87 | post TOK |
| 88 | primer pre TOK 1 |
| 89 | primer pre TOK 2 |
| 90 | primer post TOK 1 |
| 91 | primer post TOK 2 |

DETAILED DESCRIPTION OF THE INVENTION

In the framework of the present invention the following terms and definitions are used:

The term "reporter gene" in the context of present invention means that its expression results in a characteristic phenotype "reporting" its successful expression. Suitable reporters include the facultatively lethal reporters as defined herein before.

"Transformed" in the context of the present invention includes chromosomal integration and episomal expression of a particular nucleic acid sequence.

"Native" means "natural(ly)" or "naturally occurring", more specifically "naturally occurring in the specified organism" or "naturally occurring in connection with the specified gene".

A "regulatory network" in the context of present invention is a network which regulates the gene transcription ("transcriptional regulatory network") in an organism. Specifically, it is a collection of gene segments like promoters and of proteins like transcription factors controlling said promoters, which interact with each other and with other elements of a cell, thereby governing the rate and amount at which genes controlled by the network are transcribed.

A "regulatory element" is a part of said regulatory network, e.g. a promoter or transcription factor. Thus, a "regulatory element of a MDR coferring gene" may be the native promoter of said gene, e.g. P$_{PDR5}$. It may also be a transcription factor controlling the expression of said gene in its native environment, e.g. Pdr1 p, Pdr3p, Tac1p and the like.

A "comparative yeast strain" is a genetically modified yeast strain suitable as control strain in the method of present invention. It allows the exclusion of false positive results in the method of the present invention.

A "test compound" in the context of present invention is any compound which could be an inhibitor of regulatory elements within a transcriptional regulatory network and which may therefore be tested for said inhibitory effect in the method of the present invention.

A "derivative" of a chemical compound is a compound that is formed from said chemical compound or arises theoretically from said compound by replacement of at least one atom or group of atoms with another atom or group of atoms. Usually, the replaced atom or group is (part of) a functional group or is positioned at a chemically reactive center, (like, e.g., an acidic hydrogen or a hydroxy function). Common hexose derivatives are N-acetyl-hexosamines like N-acetyl-glucosamine, deoxyhexoses like deoxyglucose, etc.

In the method of embodiment (1) the regulatory element used is preferably a regulatory element of MDR conferring genes.

The method of embodiment (1) comprises in another favourable aspect
(i) the treatment of the genetically modified yeast strain (test yeast strain) with a test compound or a mixture of test compounds; and/or
(ii) determination of cell growth during or after this treatment under conditions lethal to those modified yeast cells expressing the reporter gene (preferably under control of MDR regulatory elements); and/or
(iii) identification of those test compounds allowing cell growth as inhibitors of the regulatory element.

Preferably, the method of embodiment (1) comprises steps (i) and (ii), and optionally step (iii).

One variant of this preferred aspect of embodiment (1) is its application in a way which allows the exclusion of false positive results by the parallel treatment of a comparative genetically modified yeast strain (comparative yeast strain) with the respective test compound. In said comparative yeast strain, the regulatory element is a constitutively active promoter, preferably the yeast PMA1-promoter ($P_{PMA1}$) Those test compounds allowing cell growth of the cells of the test yeast strain are inhibitors of the regulatory element if they do not allow cell growth of the comparative yeast strain cells in which the constitutively active promoter (like the PMA1-promoter) is the regulatory element.

Generally, one preferred aspect of embodiment (1) is a performance wherein the growth measurement and the identification of positives and the exclusion of false positives are carried out automatically in micro-plates using a micro-plate reader and a personal computer. The growth measurements may be carried out via measurement of the optical density at 570-600 nm of cultures grown in liquid medium and/or via comparison of colony sizes grown on solid medium.

Said above performance of embodiment (1) is especially favourable if it is designed as high throughput screening. This screening is preferably performed in micro-titre plates (96-1586 wells), which are filled with the culture medium containing the appropriate 2-DG concentration, a defined test strain inoculum and the test compound or solvent. All measurements are carried out in quadruplicates. To determine maximal growth, in a certain number of wells cells are incubated without 2-DG. To correct for media absorption, a certain number of wells is incubated with culture medium without cells. Depending on the number of repetitions per test substrate, this screening system can be up-scaled to a high throughput system testing substrate libraries in one step. After incubation of the micro-titre plates at 28° C. for 10-16 h with shaking at 900 rpm (4 mm amplitude), the optical density of the single wells is determined with a micro-titre plate reader. Alternatively, to obtain growth curves, measurements are performed every 15 min. The threshold for growth inhibition can be chosen individually between maximum and minimum growth according to the requirements of the test. The growth measurement and the identification of positives and the exclusion of false positives can be carried out manually or automatically, but preferably they are done automatically in micro-titre plates using a microtiter-plate reader and a personal computer.

The modified yeast strain used as test yeast strain and comparative yeast strain in embodiments (1) and (2), and according to embodiments (3) and (4) of the invention is preferably of the phylum Ascomycota, more preferably of the order Saccharomycetales, the family Candidaceae or the genus *Kluyveromyces*. Of these, the yeasts of the order Saccharomycetales, especially those of the family Saccharomycetaceae, are preferred. The most suitable Saccharomycetaceae are the species *Saccharomyces cerevisiae* and *Saccharomyces uvarum*, *S. cerevisiae* being preferred.

The functional nucleic acid segment which is used to transform the yeast strain of any one of embodiments (1) to (4) is episomally expressed and/or integrated into the yeast host strain's genome. Preferably, it is integrated into the yeast host strain's genome.

One aspect of embodiments (1) and (3) is the fact that any promoter of any transcriptional regulatory network can be used to control the expression of the reporter gene. Also transcription factors of the respective promoters can be cloned under the control of their own promoters. Thus, any part of the complete regulatory network can be introduced into the test yeast strains and included in the screen for inhibitors.

In a preferred aspect of embodiment (2), the test yeast strain further comprises (c) one or more additional gene(s) encoding one or more components of the regulatory network of the promoter. Said additional gene(s) (c) are preferably comprised in the functional nucleic acid segment with which the test yeast strain is transformed. More preferably, said one or more additional gene(s) encode one or more transcription factor(s) controlling said promoter. Most preferably, said transcription factors are selected from the group consisting of
(i) transcription factors regulating the expression of MDR elements in *Candida* spp. and *Saccharomyces* spp., respectively, most preferably the *C. albicans* Tac1p (Coste, A. T. et al., J. Biol. Chem. 268:19505-19511 (2004)) or other putative transcription factors activating the expression of *Candida* MDR relevant genes; and
(ii) transcription factors regulating the expression of MDR elements in mammals.

Likewise, the transcription factors controlling the promoter in the cell of embodiment (4) of the invention are preferably
(i) transcription factors regulating the expression of MDR elements in *Candida* spp. and *Saccharomyces* spp., respectively, most preferably the *C. albicans* Tac1p (Coste, A. T. et al., J. Biol. Chem. 268:19505-19511 (2004)) or other putative transcription factors activating the expression of *Candida* MDR relevant genes; and/or
(ii) transcription factors regulating the expression of MDR elements in mammals.

Figure 1:
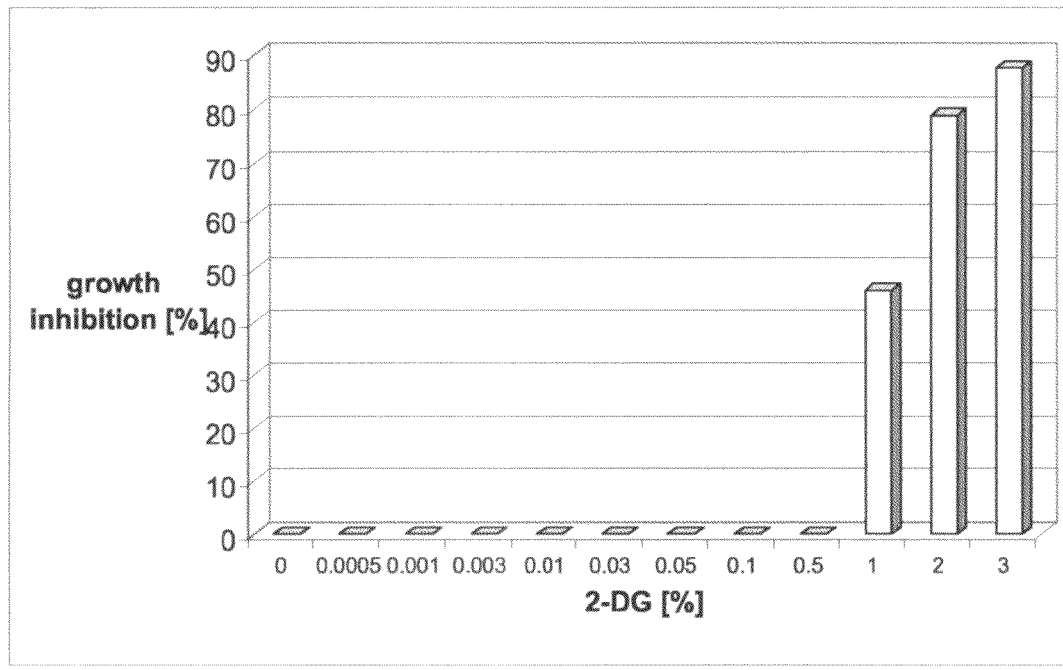
FIG. 1: Growth inhibition of S. cerevisiae strain RE700A at increasing 2-deoxy-glucose (2-DG) concentrations after incubation at 280 C for 20 h. RE700A was incubated for 20 h at 28° C. with maltose (2% (w/v)) as the sole carbon source and 2-DG at the concentrations indicated. The optical density was measured at 600 nm every 15 minutes and the integral under the growth curve was calculated. Inhibition of growth is shown in percent of growth of RE700A in the absence of 2-DG. The strain grew well in the presence of up to 0.5% (w/v) 2-DG.

In embodiment (1) or (2), the preferred yeast host strain used in the method is a mutant strain lacking genes coding for transporters, preferably hexose transporters, more preferably glucose transporters, and preferably a S. cerevisiae mutant strain. The most preferred yeast host strain in the method of said embodiments (1) and (2) and for the yeast strain of embodiment (5) (i) is the strain S. cerevisiae RE700A (see Tab.1), deprived of the seven most important glucose transporters (HXT1-7) (Reifenberger, E. et al., Molecular Microbiology 16:157-167 (1995)). The strain is not able to grow on glucose as the sole carbon source. It grows on maltose (2% (w/v)) as the sole carbon source. In addition, the strain grows well on maltose also in the presence of up to 0.5% (w/v) 2-deoxy-glucose (2-DG), a toxic glucose analogue, in the medium (FIG. 1). Growth is inhibited by 50% at a 2-DG concentration in liquid media of ~1% (w/v) (FIG. 1).

In the method according to embodiment (1) or (2), the gene encoding the facultatively lethal reporter protein is a gene encoding a protein which under certain culture conditions gives rise to a lethal phenotype (reporter gene). Preferably, said reporter gene is selected from genes encoding membrane integral proteins, more preferably from transporter genes, most preferably from hexose transporter genes including HXT1-7 and Ght1-6. Likewise, the reporter gene of embodiment (5) (ii) is a gene whose expression is facultatively lethal to the cell. "Facultatively lethal" means that the expression of the gene is lethal for the cell only under certain metabolic conditions such as incubation of the cells in the presence of certain toxic substances. Under permissive conditions the expression of the gene does not hamper the growth of the cells. Particularly preferred are genes encoding membrane integral proteins, particularly transporter protein genes including hexose transporter genes such as HXT1-7, Ght1-6 and the like.

In one preferred aspect of embodiments (1), (2) and (5)(ii) HXT7, encoding Hxt7p, a glucose transporter of S. cerevisiae, serves as reporter gene. To generate a test strain, HXT7 is (either episomally or chromosomally) introduced into S. cerevisiae RE700A under the transcriptional control of a promoter that is either the putative target for inhibitors itself or regulated by the target transcription factor and/or its respective gene promoter that is/are to be tested. Under permissive conditions, i.e. with maltose as carbon source and without 2-DG, growth of this strain is unaffected by the expression of the reporter gene HXT7. Only in the presence of a suitable 2-DG concentration in the growth medium (non-permissive conditions) the expression of HXT7 and the Hxt7p mediated 2-DG uptake inhibits cell growth. The test strain is thus easy to generate and cultivate under permissive conditions.

Other facultatively lethal genes apt for embodiments (1), (2) and (5)(ii) comprise the glucose transporter genes HXT1-7, Ght1-6 (such as Ght1, 2, 5), Glut1-2 which are lethal only if 2-deoxy-glucose is present in the medium. The Schizosaccharomyces pombe gene car1+ is facultatively lethal if expressed in S. cerevisiae cells grown in the presence of Amiloride (Jia, Z. P. et al., Mol. Gen. Genet. 241:298-304 (1993); Niederberger, C. et al., Gene 171:119-122 (1996)). S. cerevisiae gene TOK1 is facultatively lethal if S. cerevisiae cells are grown in the presence of $Cs^+$ ions (Bertl, A. et al., Molecular Microbiology 47:767-780 (2003)).

The lethal phenotype of the yeast strain according to embodiments (1) to (6) can be induced by the presence of a defined concentration of a toxic substrate of the reporter gene product in the culture/growth medium, preferably a hexose or a hexose derivative, most preferably a hexose derivative, especially 2-deoxyglucose (2-DG).

In the method of embodiment (1) and (2), the promoter (b) is preferably selected from yeast promoters and promoters controlling the expression of MDR conferring genes. Like the promoter according to embodiment (5)(iii), it includes procaryotic and eucaryotic promoters. More preferably, the promoter (b) in embodiments (1), (2) and (5)(iii) is a promoter which is part of the regulation network for MDR, most preferably a promoter which controls the expression of genes conferring drug resistance to pathogens or tumor cells. This includes promoters controlling the MDR in yeast and mammals, preferably promoters of the PDR and CDR gene families. It preferably includes promoters from Saccharomyces spp., most preferably from S. cerevisiae, especially the S. cerevisiae PDR5-promoter ($P_{PDR5}$). It furthermore preferably includes promoters from Candida spp., most preferably from C. albicans, especially the C. albicans CDR1-promoter $P_{CDR1}$ and the C. albicans CDR2-promoter $P_{CDR2}$. It further includes $P_{CaMDR}$ of C. albicans as well as the promoters of PMT gene encoding C. albicans glycosylation proteins relevant to Candida MDR, especially $P_{PMT1}$, $P_{PMT2}$ and $P_{PMT4}$, and promoters from mammalian tumor cells such as $R_{MDR1}$, $P_{MRP1-7}$.

The promoter (b) according to embodiments (1), (2) and (5)(iii) may also be a constitutively active yeast promoter, preferably a promoter driving the expression of a housekeeping gene like $P_{PMA1}$, $P_{cyc1}$ and $P_{pyk1}$ most preferably the S. cerevisiae PMA1-promoter ($P_{PMA1}$).

One aspect of embodiment (4) is the use of transcription factor genes selected from transcription factors regulating the expression of MDR elements in Candida ssp. and Saccharomyces ssp., most preferably the S. cerevisiae Pdr1 protein Pdr1p and/or the S. cerevisiae Pdr3 protein Pdr3p. Since no specific inhibitors of the MDR network in S. cerevisiae are known so far, the inhibition of two relevant transcription factors, Pdr1 p and Pdr3p, that are known to activate $P_{PDR5}$ can be mimicked by their disruption in RE700A (Example 3). This results in considerable loss of activity of $P_{PDR5}$. Thus, if an inhibitor of transcription factors or of the expression of those transcription factors needed to activate the promoter controlling the reporter gene is applied to the modified yeast cell according to embodiment (4) it can be identified as potential MDR inhibitor using the method of embodiment (1).

In the yeast strain according to any one of embodiments (1) to (5) the functional nucleic acid segment may further carry functional sequences selected from marker genes, including fluorescence markers such as GFP and GFP derivatives, resistance markers, splice donor and acceptor sequences, etc.

In the method according to embodiments (1) and (2) the test yeast strain is in a preferred aspect a S. cerevisiae RE700A strain comprising HXT7 as reporter gene. Yeast strains used in embodiments (1) and (2), and according to embodiment (3) in their most preferred aspect are S. cerevisiae RE700A strains comprising HXT7 as reporter gene under the control of promoters or transcription factors of genes selected from the group consisting of MDR conferring genes and constitutively active yeast promoters. Of said strains, the strains as listed in Table 1 are even more preferred, especially the ones selected from the group consisting of RE700A e $P_{PDR5}$-HXT7 (ET[PDR]), RE700A e $P_{CDR1-HXT}7$ (ET[CDR1]), RE700A e $P_{CDR2}$-HXT7 (ET[CDR2]), RE700A e $P_{CUP}$-HXT7 (ECFP), RE700A i $P_{PDR5}$-HXT7 (IT[PDR]), RE700A i $P_{CDR1}$-HXT7 (IT[CDR1]), RE700A i $P_{CDR2}$-HXT7 (IT[CDR2]), RE700A i $P_{PMA1}$-HXT7 (ICFP), RE700A Δpdr1 tok1::$P_{PDR5}$-HXT7, RE700A Δpdr3 tok1::$P_{PDR5}$-HXT7, and RE700A Δpdr1 Δpdr3 tok1::$P_{PDR5}$-HXT7.

TABLE 1

Constructed strains: The parental strains and the plasmids that were used for transformation are listed. The names and abbreviations of the newly generated strains are given in the third column. In addition the respective genotypes are shown in the utmost right column.

| Strain transformed | with plasmid | yielding | genotype |
|---|---|---|---|
| RE700A | | | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 |
| RE700A | pY-$P_{PDR5}$-HXT7 | RE700A e $P_{PDR5}$-HXT7 (ET[PDR]) | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 [pY-$P_{PDR5}$-HXT7] |
| RE700A | pY-$P_{CDR1}$-HXT7 | RE700A e $P_{CDR1}$-HXT7 (ET[CDR1]) | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3[pY-$P_{CDR1}$-HXT7] |
| RE700A | pY-$P_{CDR2}$-HXT7 | RE700A e $P_{CDR2}$-HXT7 (ET[CDR2]) | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3[pY-$P_{CDR2}$-HXT7] |
| RE700A | pY-$P_{PDR5}$-GFP | RE700A e $P_{PDR5}$-GFP (CQ[PDR]) | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3[pY-$P_{PDR5}$-GFP] |
| RE700A | pY-$P_{CDR1}$-GFP | RE700A e $P_{CDR1}$-GFP (CQ[CDR1]) | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3[pY-$P_{CDR1}$-GFP] |
| RE700A | pY-$P_{CDR2}$-GFP | RE700A e $P_{CDR2}$-GFP (CQ[CDR2]) | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3[pY-$P_{CDR2}$-GFP] |
| RE700A | pY-$P_{CUP}$-HXT7 | RE700A e $P_{CUP}$-HXT7 (ECFP) | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3[pY-$P_{CUP}$-HXT7] |
| RE700A | p77t-(ura)-$P_{PDR5}$-HXT7 | RE700A i $P_{PDR5}$-HXT7 (IT[PDR]) | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 tok1::$P_{PDR5}$HXT7 |
| RE700A | p77t-(ura)-$P_{CDR1}$-HXT7 | RE700A i $P_{CDR1}$-HXT7 (IT[CDR1]) | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 tok1::$P_{CDR1}$HXT7 |
| RE700A | p77t-(ura)-$P_{CDR2}$-HXT7 | RE700A i $P_{CDR2}$-HXT7 (IT[CDR2]) | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 tok1::$P_{CDR2}$HXT7 |
| RE700A | p77t-(ura)-$P_{PMA1}$-HXT7 | RE700A i $P_{PMA1}$-HXT7 (ICFP) | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 tok1::$P_{PMA1}$HXT7 |
| RE700A | pUG6-Δpdr1 | RE700A Δpdr1 | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 Δpdr1 |
| RE700A Δpdr1 | pY-$P_{PDR5}$-GFP | RE700A Δpdr1 [pY-$P_{PDR5}$-GFP] | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 Δpdr1[pY-$P_{PDR5}$-GFP] |
| RE700A Δpdr1 | p77t-(ura)-$P_{PDR5}$-HXT7 | RE700A Δpdr1 tok1::$P_{PDR5}$-HXT7 | MATa ura3-52 his3-11,15 lue2-3,112 MAL2 SUC2 GAL MEL |

TABLE 1-continued

Constructed strains: The parental strains and the plasmids that were used for transformation are listed. The names and abbreviations of the newly generated strains are given in the third column. In addition the respective genotypes are shown in the utmost right column.

| Strain transformed | with plasmid | yielding | genotype |
|---|---|---|---|
| RE700A | pUG6-Δpdr3 | RE700A Δpdr3 | hxt1Δ::HIS3::Δhxt4 hxt5::LEU2 hxt2Δ::HIS3 hxt3Δ::LEU2::Δhxt6 hxt7::HIS3 Δpdr1 tok::$P_{PDR5}$-HXT7 MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 Δpdr3 |
| RE700A Δpdr3 | pY-$P_{PDR5}$-GFP | RE700A Δpdr3 [pY-$P_{PDR5}$-GFP] | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 Δpdr3[pY-$P_{PDR5}$-GFP] |
| RE700A Δpdr3 | p77t-(ura)-$P_{PDR5}$-HXT7 | RE700A Δpdr3 tok1::$P_{PDR5}$-HXT7 | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 Δpdr3 tok::$P_{PDR5}$-HXT7 |
| RE700A Δpdr1 | pUG6-Δpdr3 | RE700A Δpdr1 Δpdr3 | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 Δpdr1 Δpdr3 |
| RE700A Δpdr1 Δpdr3 | pY-$P_{PDR5}$-GFP | RE700A Δpdr1 Δpdr3 [pY-$P_{PDR5}$-GFP] | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 Δpdr1 Δpdr3[pY-$P_{PDR5}$-GFP] |
| RE700A Δpdr1 Δpdr3 | p77t-(ura)-$P_{PDR5}$-HXT7 | RE700A Δpdr1 Δpdr3 tok1:: $P_{PDR5}$-HXT7 | MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 Δpdr1 Δpdr3 tok::$P_{PDR5}$-HXT7 |
| RE700A | p77t-(ura)-$P_{PDR5long}$-HXT7 | RE700A tok1::$P_{PDR5long}$-HXT7 | MATa ura3-52 his3-11,15 leu2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 tok1::URA3, $P_{PDR5long}$-HXT7 |
| RE700A Δpdr1 | p77t-(ura)-$P_{PDR5long}$-HXT7 | RE700A Δpdr1 tok1::$P_{PDR5long}$-HXT7 | MATa ura3-52 his3-11,15 leu2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 Δpdr1 tok1::URA3, $P_{PDR5long}$-HXT7 |
| RE700A Δpdr3 | p77t-(ura)-$P_{PDR5long}$-HXT7 | RE700A Δpdr3 tok1::$P_{PDR5long}$-HXT7 | MATa ura3-52 his3-11,15 leu2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 Δpdr3 tok1::URA3, $P_{PDR5long}$-HXT7 |
| RE700A Δpdr1,3 | p77t-(ura)-$P_{PDR5long}$-HXT7 | RE700A Δpdr1,3 tok1::PPDR5long-HXT7 | MATa ura3-52 his3-11,15 leu2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 Δpdr1,3 tok1::URA3, $P_{PDR5long}$-HXT7 |

The integration vector of embodiment (7) of the invention comprises the functional nucleic acid segment as defined in connection with embodiments (3) to (6). Preferably, the integration vector is suitable for chromosomal integration, and in addition the functional nucleic acid segment is preferably flanked by sequences homologous to the target site DNA sequences in the host strain.

The method according to embodiment (8) of the invention comprises the inserting of a gene cassette into the yeast genome using an integration vector according to embodiment (7). The yeast transformation can be effected in accordance with the lithium acetate method as described by R. Rothstein in Methods in Enzymology 194:281-302 (1991). Yeast genetic methods, especially for *S. cerevisiae*, are in accordance with the methods described in F. Sherman et al., Cold Spring Harbor Laboratory, Cold Spring Harbor, N.Y. (1981). The integration is preferably followed by means of selection, in one preferred aspect by growth on media lacking uracil. Correct integration is proved by means of diagnostic PCR and Southern blotting.

One aspect of embodiment (8) is the introduction of the gene cassette comprising the reporter gene and the promoter into a chromosomal gene locus of the host cell. This can be done by recombinant DNA methods introducing selectable marker genes at the same time. Preferred marker genes are coding for proteins conferring resistances and/or auxotrophic needs, especially the auxotrophy markers URA3 and LEU2 or genes conferring resistance to G418 (aminoglycosid phosphotransferase gene). Constructs comprising those marker genes together with the gene cassette to be transferred can be linearized and introduced into the yeast host cell. There they will replace the wild type loci by homologous recombination. The strains bearing the modified loci can then be found by selection on the marker gene. Preferred yeast loci for introduction of those genes are single copy genes, the most preferred locus is the tok1 locus. TOK1 gene is a single copy gene coding for potassium channels in yeast. Its replacement by homologous recombination was first described in WO 03/031600.

One aspect of the test system of embodiment (1) is the use of a S. cerevisiae cell line with an episomally introduced reporter gene. Preferably a cell line comprising a reporter gene under control of one of the S. cerevisia MDR regulatory network promoters is used, most preferably a strain comprising the HXT7 gene. Especially preferred is the use of the test strain ET[PDR] (see Table 1).

Figure 3:
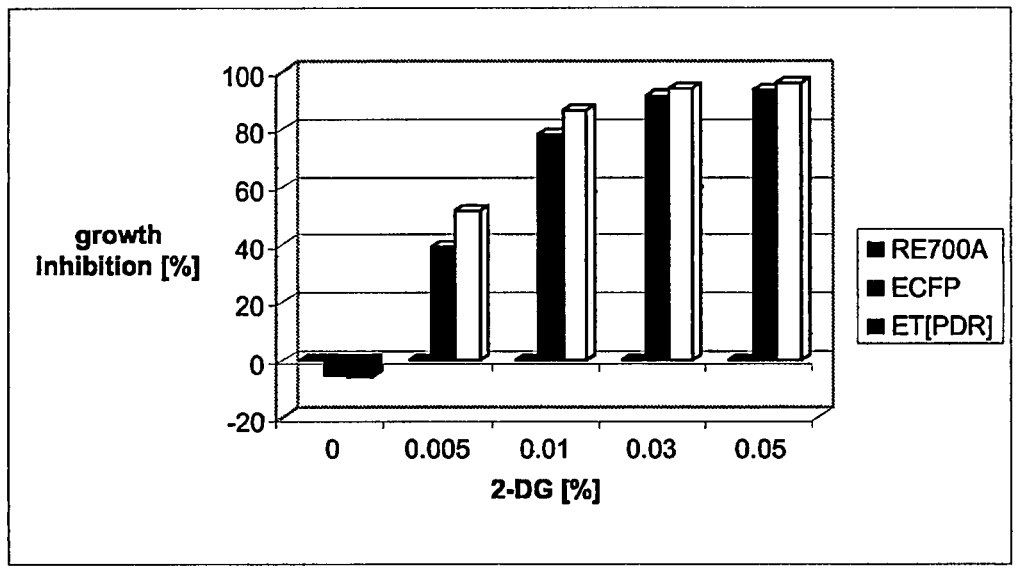
FIG. 3: Growth inhibition of RE700A, ECFP, ET[PDR], ICFP and IT[PDR] at increasing 2-DG concentrations after 20 h incubation at 28° C.
Figure 3:
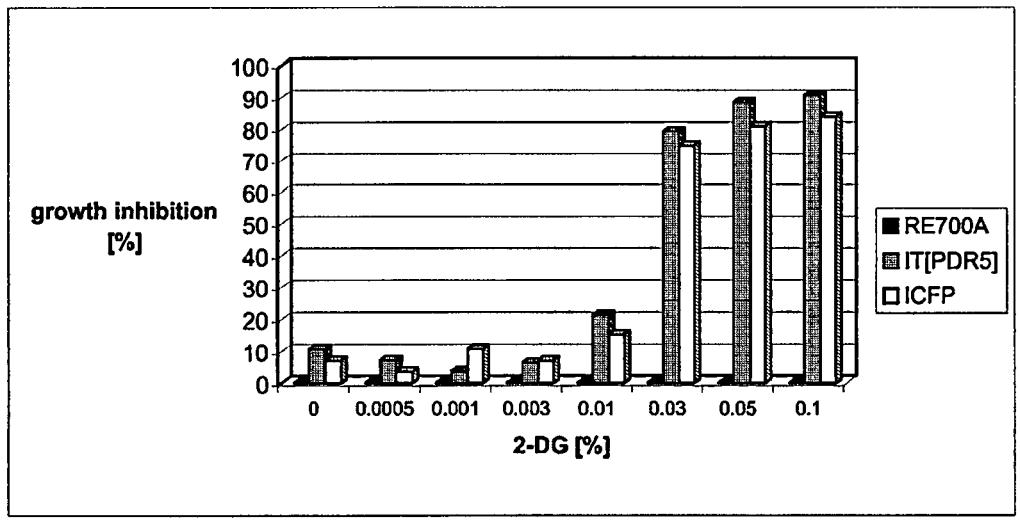

To screen for inhibitors of the S. cerevisia MDR regulatory network the test strain ET[PDR] can be incubated in selective YNB medium with 2% (w/v) maltose as the carbon source and 0.03% (w/v) 2-DG. Under these non-permissive conditions the growth of the test strain ET[PDR] was inhibited when $P_{PDR5}$ was active (FIG. 3). Test compounds dissolved in solvent or solvent alone are added and growth is analysed. ET[PDR] will grow under non-permissive conditions (primary positive result) only when the test compound inhibits one (or more) crucial component(s) of the S. cerevisia MDR network (true positive result), or if the activity of the reporter gene product Hxt7p is directly inhibited by this compound (false positive result).

If desired, RE700A can also be grown under the conditions described above (i.e. YNB medium+2% (w/v) maltose+ 0.03% (w/v) 2-DG, without compound but with solvent) to determine maximal growth, corresponding to a complete inhibition of Hxt7p function.

Since unspecific metabolic inhibitors do not allow cell growth and thus will not be detected, the number of false positive results is very low. To further exclude false positive results, compounds that lead to primary positive results are re-checked using the protocol described above, but with strain ECFP instead of ET[PDR]. In the case that ECFP cells grow in the presence of test compound under non-permissive conditions, this compound gave a false positive result. If desired the inhibitory efficacy of the compound is determined by using CQ[PDR]: Strain CQ[PDR] is incubated in selective YNB medium with 2% (w/v) maltose as the carbon source and 0.03% (w/v) 2-DG. The test compound dissolved in solvent or solvent alone is added and the decrease of GFP fluorescence induced by the compound is quantified.

Another aspect of the test system of embodiment (1) is the use of a S. cerevisiae cell line with an chromosomally introduced reporter gene. Preferably a cell line comprising a reporter gene under control of one of the S. cerevisia MDR regulatory network promoters is used, most preferably a strain comprising the HXT7 gene. Especially preferred is the use of the test strain IT[PDR] (see Table 1).

To screen for inhibitors of the S. cerevisia MDR regulatory network the test strain IT[PDR] can be incubated in YNB medium with 2% (w/v) maltose as the carbon source and 0.05% (w/v) 2-DG. Under these non-permissive conditions the growth of the test strain IT[PDR] was inhibited when $P_{PDR5}$ was active (FIG. 3). Test compounds dissolved in solvent or solvent alone are added and growth is analysed. IT[PDR] will grow under non-permissive conditions (primary positive result) only when the test compound inhibits one (or more) crucial component(s) of the S. cerevisia MDR network (true positive result), or if the activity of the reporter gene product Hxt7p is directly inhibited by this compound (false positive result).

If desired, RE700A can also be grown under the conditions described above (i.e. YNB medium+2% (w/v) maltose+ 0.05% (w/v) 2-DG, without compound but with solvent) to determine maximal growth, corresponding to a complete inhibition of Hxt7p function.

Since unspecific metabolic inhibitors do not allow cell growth and will thus not be detected, the number of false positive results is expected to be very low. To further exclude false positive results, compounds that lead to primary positive results are re-checked using the protocol described above, but with strain ICFP instead of IT[PDR]. In the case that ICFP cells grow in the presence of test compound under non-permissive conditions, this compound gave a false positive result. If desired the inhibitory efficacy of the compound is determined by using CQ[PDR]: Strain CQ[PDR] is incubated in selective YNB medium with 2% (w/v) maltose as the carbon source and 0.05% (w/v) 2-DG. The test compound dissolved in solvent or solvent alone are added and the decrease of GFP fluorescence induced by the compound is quantified.

Another preferred aspect of the use of a S. cerevisiae cell line with an episomally introduced reporter gene in the test system of embodiment (1) is the use of a cell line comprising a reporter gene under control of one of the C. albicans MDR regulatory network promoters, most preferably a strain comprising the HXT7 gene. Especially preferred is the use of the test strain ET[CDR1] (see Table 1).

To screen for inhibitors of the $P_{CDR1}$, the test strain ET[CDR1] can be incubated in selective YNB medium with 2% (w/v) maltose as the carbon source and 0.05% (w/v) 2-DG. Under these non-permissive conditions the growth of the test strain ET[CDR1] was inhibited when $P_{CDR1}$ was active (FIG. 6). Test compounds dissolved in solvent or solvent alone are added and growth is analysed. ET[CDR1] will grow under non-permissive conditions (primary positive result) only when the test compound inhibits $P_{CDR1}$ (true positive result), or if the activity of the reporter gene product Hxt7p is directly inhibited by this compound (false positive result).

If desired, RE700A can also be grown under the conditions described above (i.e. YNB medium+2% (w/v) maltose+ 0.05% (w/v) 2-DG, without the test compound but with solvent) to determine maximal growth, corresponding to a complete inhibition of Hxt7p function.

Since unspecific metabolic inhibitors do not allow cell growth and thus, will not be detected, the number of false positive results is expected to be very low. To further exclude false positive results, compounds that lead to primary positive results are re-checked using the protocol described above, but with strain ECFP instead of ET[CDR1]. In the case that ECFP cells grow in the presence of test compound under non-permissive conditions, this compound gave a false positive result. If desired the inhibitory efficacy of the test compound is determined by using CQ[CDR1]: Strain CQ[CDR1] is incubated in selective YNB medium with 2% (w/v) maltose as the carbon source and 0.05% (w/v) 2-DG. The test compound dissolved in solvent or solvent alone are added and the decrease of GFP fluorescence induced by the compound is quantified.

Another preferred aspect of the use of a *S. cerevisiae* cell line with an episomally introduced reporter gene in the test system of embodiment (1) is the use of a cell line comprising a reporter gene under control of one of the *C. albicans* MDR regulatory network promoters, most preferably a strain comprising the HXT7 gene. Especially preferred is the use of the test strain ET[CDR2] (see Table 1).

To screen for inhibitors of the $P_{CDR1}$, the test strain ET[CDR2] can be incubated in selective YNB medium with 2% (w/v) maltose as the carbon source and 0.2% (w/v) 2-DG. Under these non-permissive conditions the growth of the test strain ET[CDR2] was inhibited when $P_{CDR1}$ was active (FIG. 6). Test compounds dissolved in solvent or solvent alone are added and growth is analysed. ET[CDR2] will grow under non-permissive conditions (primary positive result) only when the test compound inhibits $P_{CDR1}$ (true positive result), or if the activity of the reporter gene product Hxt7p is directly inhibited by this compound (false positive result).

If desired, RE700A can also be grown under the conditions described above (i.e. YNB medium+2% (w/v) maltose+0.2% (w/v) 2-DG, without the test compound but with solvent) to determine maximal growth, corresponding to a complete inhibition of Hxt7p function.

Since unspecific metabolic inhibitors do not allow cell growth and thus, will not be detected, the number of false positive results is expected to be very low. To further exclude false positive results, compounds that lead to primary positive results are re-checked using the protocol described above, but with strain ECFP instead of ET[CDR2]. In the case that ECFP cells grow in the presence of test compound under non-permissive conditions, this compound gave a false positive result. If desired the inhibitory efficacy of the test compound is determined by using CQ[CDR2]: Strain CQ[CDR2] is incubated in selective YNB medium with 2% (w/v) maltose as the carbon source and 0.2% (w/v) 2-DG. The test compound dissolved in solvent or solvent alone are added and the decrease of GFP fluorescence induced by the compound is quantified.

Another preferred aspect of the use of a *S. cerevisiae* cell line with a chromosomally introduced reporter gene in the test system of embodiment (1) is the use of a cell line comprising a reporter gene under control of one of the *C. albicans* MDR regulatory network promoters, most preferably a strain comprising the HXT7 gene. Especially preferred is the use of the test strain IT[CDR1] (see Table 1).

To screen for inhibitors of $P_{CDR1}$, the test strain IT[CDR1] is incubated in YNB medium with 2% (w/v) maltose as the carbon source and 0.03% (w/v) 2-DG. Under these non-permissive conditions the growth of the test strain IT[CDR1] is inhibited when $P_{CDR1}$ is active. Test compounds dissolved in solvent or solvent alone are added and growth is analysed. IT[CDR1] will grow under non-permissive conditions (primary positive result) only when the test compound inhibits $P_{CDR1}$ (true positive result), or if the activity of the reporter gene product Hxt7p is directly inhibited by this compound (false positive result).

If desired, RE700A can also be grown under the conditions described above (i.e. YNB medium+2% (w/v) maltose+ 0.03% (w/v) 2-DG, without test compound but with solvent) to determine maximal growth, corresponding to a complete inhibition of Hxt7p function.

Since unspecific metabolic inhibitors do not allow cell growth and thus, will not be detected, the number of false positive results is expected to be very low. To further exclude false positive results, compounds that lead to primary positive results are re-checked using the protocol described above, but with strain ECFP instead of IT[CDR1]. In the case that ECFP cells grow in the presence of the test compound under non-permissive conditions, this compound gave a false positive result.

Another preferred aspect of the use of a *S. cerevisiae* cell line with a chromosomally introduced reporter gene in the test system of embodiment (1) is the use of a cell line comprising a reporter gene under control of one of the *C. albicans* MDR regulatory network promoters, most preferably a strain comprising the HXT7 gene. Especially preferred is the use of the test strain IT[CDR2] (see Table 1).

To screen for inhibitors of $P_{CDR2}$, the test strain IT[CDR2] is incubated in selective YNB medium with 2% (w/v) maltose as the carbon source and 2% (w/v) 2-DG. Under these non-permissive conditions the growth of the test strain IT[CDR2] is inhibited when $P_{CDR2}$ is active (FIG. 8). Test compounds dissolved in solvent or solvent alone are added and growth is analysed. IT[CDR2] will grow under non-permissive conditions (primary positive result) only when the test compound inhibits $P_{CDR2}$ (true positive result), or if the activity of the reporter gene product Hxt7p is directly inhibited by this compound (false positive result).

If desired, RE700A can also be grown under the conditions described above (i.e. YNB medium+2% (w/v) maltose+1-2% (w/v) 2-DG, without compound but with solvent) to determine maximal growth, corresponding to a complete inhibition of Hxt7p function.

Since unspecific metabolic inhibitors do not allow cell growth and thus, will not be detected, the number of false positive results is expected to be very low. To further exclude false positive results, compounds that lead to primary positive results are re-checked using the protocol described above, but with strain ECFP instead of IT[CDR2]. In the case that ECFP cells grow in the presence of test compound under non-permissive conditions, this compound gave a false positive result.

For further screens for inhibitors of the *Candida albicans* MDR transcription factor Tac1p (Coste, A. T. et al., J. Biol. Chem. 268:19505-19511 (2004)) or yet unknown *C. albicans* transcription factors these will have to be co-expressed in the test strains described above.

The kit of embodiment (10) may further comprise a comparative yeast strain as defined above and/or culture media for the test yeast strain and/or the comparative yeast strain.

The *S. cerevisiae* mutant strain RE700A i $P_{PDR5}$-HXT7 (MATa ura3-52 his3-11,15 lue2-3,112 MAL2 SUC2 GAL MEL hxt1Δ:: HIS3::Δhxt4 hxt5:: LEU2 hxt2Δ::HIS3 hxt3Δ:: LEU2::Δhxt6 hxt7::HIS3 tok1::$P_{PDR5}$HXT7; also referred to as RE700A i PPDR5-HXT7) was deposited at the DSMZ, Deutsche Sammlung von Mikroorganismen und Zellkulturen GmbH, Mascheroder Weg 1 b, 38124 Braunschweig, Germany, as DSM 16852 on Nov. 3, 2004.

In the following examples, material and methods of the present invention are provided. It should be understood that these examples are for illustrative purpose only and are not to be construed as limiting this invention in any manner. All publications, patents, and patent applications cited herein are hereby incorporated by reference in their entity for all purposes.

EXAMPLES

General Methods/Materials

Media: YNB-medium: 1.7 g/l Yeast Nitrogen Base without amino acids and ammonium sulfate, 5 g/l ammonium sulfate, 0.5 g/l amino acid drop out mix (composition: 150 mg lysine, 300 mg valine, 150 mg tyrosine, 500 mg threonine, 500 mg serine, 250 mg phenylalanine, 100 mg arginine, 100 mg methionine, 500 mg tryptophane, 250 mg adenine, 100 mg asparagine, 100 mg glutamic acid).

+glucose/maltose: 20 g/l.

Strain growth: The growth of the strains in liquid medium was determined by measuring the optical density at 600 nm. To obtain growth curves, measurements were performed every 15 min. Alternatively, start and endpoint (after 12-16 h) measurements were carried out.

Recombinant DNA technology: For the enrichment and manipulation of DNA, standard methods were employed as described in Sambrook, J. et al., Cold Spring Harbor Laboratory Press, Cold Spring Harbor, N.Y. (1989). The molecular-biological reagents used were employed according to the manufacturer's instructions.

Example 1

Construction of Plasmids and Strains

To express the S. cerevisiae HXT7 gene in the S. cerevisiae mutant strain RE700A under the control of different promoters, multicopy plasmids and integration cassettes were constructed. To delete the PDR1 and/or PDR3 genes from the RE700A genome, deletion cassettes were constructed. In addition, control plasmids and control integration cassettes were constructed.

(A) Polymerase Chain Reaction (PCR)

Genomic DNA from S. cerevisiae strain PLY 232 (Bertl, A. et al. Molecular Microbiology 47:767-780 (2003)) was isolated using standard protocols (Sambrook, J. et al., Cold Spring Harbour Laboratory Press (1989)). 500 ng of chromosomal DNA were used in polymerase chain reactions (PCR) to obtain the desired DNA fragments. PCR conditions were as follows:

Step 1: denaturation; 2 min 95° C.

Step 2: denaturation; 20 s 94° C.

Step 3: annealing; 45 s 55° C.

Step 4: elongation; 2 min/kb length of fragment to be amplified 72° C.

Step 5: elongation; 5 min 72° C.

Repeat steps 2-4 30 times
Thermostable DNA polymerase: Pwo-Polymerase

HXT7: To amplify the HXT7 gene (NCBI geneID: 851943, NC_001136 chromosome IV, 1154208-1155920, complementary) (PCR-HXT7; SEQ ID NO:1) the oligonucleotides 5'GAGA GCATGCGGATCCACCATGTCACAAGACGCTGCTA TTGC (SEQ I D NO:2), position 1-23 referring to the coding sequence of HXT7 and 5'GAGA CTGCAGTTATTTGGTGCTGAACATCTC (SEQ ID NO:3), position 1692-1713 referring to the HXT7 coding sequence, were used as primers in a PCR. Additional nucleotides are typed in italics, restriction sites that were introduced to facilitate cloning (SphI and BamHI [SEQ ID. NO:2] and PstI [SEQ ID. NO:3], respectively) are underlined.

PDR5 promoter: To amplify the promoter of PDR5 ($P_{PDR5}$) (NC_001147, S. cerevisiae chromosome XV, 619480-619839) (PCR-$P_{PDR5}$; SEQ ID NO:4) the oligo-nucleotides 5'GAGACTCGAGGATCTGTATTCCTACTTATG (SEQ ID NO:5), position −360−−341 referring to the coding sequence of PDR5 (SEQ ID NO:6) (NCBI geneID: 854324, NC_001147, S. cerevisiae chromosome XV, 619840-624375) and 5'GAGA GGATCCTTTTGTCTAAAGTCTTTCGAACG (SEQ ID NO:7), position −23−−1 referring to the coding sequence of PDR5 were used. Additional nucleotides are typed in italics, restriction sites that were introduced to facilitate cloning (XhoI and BamHI, respectively) are underlined.

Target region pre PDR1: To amplify the target regions pre PDR1 (NC_001139, S. cerevisiae chromosome VII, 472304-472719) (PCR-pre-PDR1; SEQ ID NO:8) the oligo-nucleotides 5'GAGA CGTACGCGATCGCGTAATACCGGCAATTACGG (SEQ ID NO:9), position −416−−390 referring to the coding sequence of PDR1 (SEQ ID NO:10) (NCBI geneID: 852871, NC_001139, S. cerevisiae chromosome VII, 469097-472303, complementary) and 5'GAGA GTCGACCTTCCAGTTTCTTGGATTCTT TTCTG-TATATTC (SEQ ID NO:11), position −33−−1 referring to the coding sequence of PDR1 were used. Additional nucleotides are typed in italics, restriction sites that were introduced to facilitate cloning (BsiWI and SalI, respectively) are underlined.

Target region post PDR1: To amplify the target regions post PDR1 (NC_001139, S. cerevisiae chromosome VII, 468830-469194) (PCR-post-PDR1; SEQ ID NO:12) the oligo-nucleotides 5'CGCAAGTCCAATCTAATAAACCAATCAATGC (SEQ ID NO: 13), position 2941-2971 referring to the coding sequence of PDR1 and 5'GAGA CCGCGGAGTTTAGCTTTTTTTACGTTAGCCTC (SEQ ID NO:14), position +3448-+3473 referring to the coding sequence of PDR1, were used. Additional nucleotides are typed in italics, restriction site (SacI I) is underlined.

Target region pre PDR3: To amplify the target region pre PDR3 (NC_001134, S. cerevisiae chromosome II, 217153-217472) (PCR-pre-PDR3; SEQ ID NO:15) the oligo-nucleotides 5'GAGA CGTACGCACCGTGCTCTGCTGCTTTCAGG (SEQ ID NO:16), position −320−−297 referring to the coding sequence of PDR3 (SEQ ID NO: 17) (NCBI geneID: 852278, NC_001134, S. cerevisiae chromosome II, 217473-220403) and 5'GAGA GTCGACTGCGGTCACGCAATAAGAAAAAATTAA TAAAAC (SEQ ID NO:18), position −33−−1 referring to the coding sequence of PDR3 were used. Additional nucleotides are typed in italics, restriction sites that were introduced to facilitate cloning (BsiWI and SalI, respectively) are underlined. Pre PDR3 is the 5'-non-coding region of the PDR3 gene.

Target region post PDR3: To amplify the target region post PDR3 (NC-001134, S. cerevisiae chromosome II, 220404-220799) (PCR-post-PDR3; SEQ ID NO:19) the oligo-nucleotides 5' GAGA ACTAGTAAACGCAAAAGAAATAGGGAAGCAGA GCATAACC (SEQ ID NO:20), position +2921-+2964 referring to the coding sequence of PDR3 and 5'GAGA GTTAACCGCAACGGCAGCAGAATAGAGAAAGCG (SEQ ID NO:21), position +3300-+3326 referring to the coding sequence of PDR3 were used. Additional nucleotides are typed in italics, restriction sites that were introduced to facilitate cloning (SpeI and HpaI, respectively) are underlined. Post PDR3 is the 3'-non-coding region of PDR3.

Ura3 gene: 100 ng of pYEX™-BX (SEQ ID NO: 22) (Clontech) plasmid DNA was used as template in a PCR to amplify the UR43 gene (NCBI geneID: 856692, NC_001137, *S. cerevisiae* chromosome V, 116167-116970) (PCR-URA3; SEQ ID NO:23), employing oligo-nucleotides 5'GAGAGCCGGCCAAGAATTAGCTTTTCAATTCA ATCC (SEQ ID NO:24), binding at position 2473-2498 of pYEX-BX and 5'GAGAGACGTCGGGTAATAACT-GATATAATTAAATTG (SEQ ID NO:25), binding at position 1383-1408 of pYEX-BX. The coding sequence of URA3 is located at position 1464-2264 of pYEX-BX. UR43 is a biosynthetic *S. cerevisiae* gene coding for the orotidine-5'-phosphate decarboxylase.

*Candida albicans* CDR1 and CDR2 promoters: 500 ng of *Candida albicans* genomic DNA was used in a PCR to amplify the promoters of CDR1 ($P_{CDR1}$) and CDR2 ($P_{CDR2}$)

To amplify $P_{CDR1}$ (NCBI X77589, 1-1136) (PCR-$P_{CDR1}$; SEQ ID NO:26) the oligo-nucleotides 5'GAGAC TCGAGGGATCCTCGTTACTCAATAAGT (SEQ ID NO:27), position −1211−−1189 referring to the coding sequence of CDR1 (SEQ ID NO:28) (NCBI X77589, 1211-5716) and 5'GAGA TGATCAGCATGCGTGATATAAAAGAATAAA ATGG (SEQ ID NO:29), position −52−−75 referring to the coding sequence of CDR1 were used. Additional nucleotides are typed in italics, restriction sites that were introduced to facilitate cloning (XhoI, BclI and SphI, respectively) are underlined. To amplify $P_{CDR2}$ (NCBI U63812, 1-900) (PCR-$P_{CDR2}$; SEQ ID NO:30) the oligo-nucleotides 5'GAGAC TCGAGGGTTCCTCTAAATAAAAACTAG (SEQ ID NO:31), position −901−−879 referring to the coding sequence of CDR2 (SEQ ID NO:32) (NCBI U63812, 902-5401) and 5'GAGAGGATCCATGTTTTTATTGTATGTGTTAATTAG (SEQ ID NO:33), position −28-1 referring to the coding sequence of CDR2 were used. Additional nucleotides are typed in italics, restriction sites that were introduced to facilitate cloning (XhoI and BamHI, respectively) are underlined.

(B) Construction of Plasmids

All fragments obtained in and used for subsequent steps were separated by agarose gel electrophoresis and eluted from the gel matrix after digestion/before further use.

Episomally Replicating Plasmids:

To obtain the (control) plasmid pY-$P_{PDR5}$-GFP (SEQ ID NO:34) (FIG. 9), the PCR-product PCR-$P_{PDR5}$ (SEQ ID NO:4) was digested with XhoI and BamHI. The resulting 0.366 kb fragment was ligated to the 7.845 kb XhoI I BamHI fragment from pYEX-BX-rad54/GFP (SEQ ID NO:35) (Lichtenberg-Fraté, H. et al., Toxicology in Vitro 17:709-716 (2003)).

To episomally express HXT7 in RE700A under the control of $P_{PDR5}$ the multicopy plasmid pY-$P_{PDR5}$-HXT7 (SEQ ID NO:36) (FIG. 10) was used. To obtain this plasmid, the PCR-product PCR-HXT7 (SEQ ID NO:1) was digested with BamHI and PstI. The 1.726 kb fragment was ligated to a 7.253 kb fragment, that was obtained from pY-$P_{PDR5}$-GFP (SEQ ID NO:34) after digestion with BamHI and PstI.

To episomally express HXT7 in RE700A under the control of $P_{CDR1}$ the multicopy plasmid pY-$P_{CDR1}$-HXT7 (SEQ ID NO:37) (FIG. 10) was used. To obtain this plasmid, the PCR-product PCR-HXT7 (see above) was digested with SphI and PstI, the resulting 1.728 kb fragment was ligated to the 8.044 kb fragment obtained from pY-$P_{CDR1}$-GFP (SEQ ID NO:38) (FIG. 9) after digestion with SphI and PstI. The plasmid pY-$P_{CDR1}$-GFP was constructed by ligation of the 1.159 kb fragment of the PCR-product PCR-$P_{CDR1}$ (SEQ ID NO:26), obtained after digestion with BclI and XhoI to the 7.844 kb BamHI I XhoI fragment from pY-$P_{PDR5}$-GFP (SEQ ID NO:34).

For episomal expression of HXT7 under control of $P_{CDR2}$ the plasmid pY-$P_{CDR2}$-HXT7 (SEQ ID NO:39) (FIG. 10) was used. The PCR-product PCR-HXT7 (SEQ ID NO:1) was digested with BamHI and PstI to get a 1.726 kb fragment that was ligated to the 7.794 kb fragment Of pY-$P_{CDR2}$-GFP (SEQ ID NO:40), obtained after digestion of this plasmid with BamHI and PstI. The plasmid pY-$P_{CDR2}$-GFP (FIG. 9) was obtained by ligation of the 0.907 kb BamHI/XhoI fragment from the PCR-product PCR-$P_{CDR2}$ (SEQ ID NO:30) to the 7.844 kb BamHI/XhoI from digested pY-$P_{PDR5}$-GFP (SEQ ID NO: 34).

For episomal expression of HXT7 under the control of $P_{CUP1}$ the plasmid PY-$P_{CUP1}$-HXT7 (SEQ ID NO:41) (FIG. 10) was used. The PCR-product PCR-HXT7 (SEQ ID NO: 1) was digested with BamHI and PstI to get a 1.726 kb fragment that subsequently was ligated to the 7.112 kb fragment obtained from pYEX-BX-GFP (SEQ ID NO:42), after digestion with BamHI and PstI.

Integration Plasmids:

For integration of HXT7 in the genome of *S. cerevisiae* RE700A under the control of diverse promoters and for the generation of control strains the TOK1 (SEQ ID NO:43) (NCBI geneID: 853352, NC_001142, *S. cerevisiae* chromosome X, 254653-256728) integration plasmids were constructed.

p77t-(ura) (SEQ ID NO:45): The plasmid p77x (identical with p77-tok-pma1, H. Lichtenberg, J. Ludwig, PCT WO 03/031600 A1) (SEQ ID NO:44) was digested with NaeI and AatII. The resulting 4.568 kb fragment was ligated to the 1.124 kb fragment obtained by digestion of the PCR product PCR-URA3 (SEQ ID NO:23) with NaeI and AatII.

p77t-(ura)-w/o-prom (SEQ ID NO:47): p77x (SEQ ID NO:44) was digested with SalI, and ApaI. The sticky ends of the resulting 6.506 kb fragment were blunted by treatment with T4-DNA polymerase followed by self ligation resulting in p77t-w/o-prom (SEQ ID NO:46). The 2.832 kb fragment obtained from p77t-w/o-prom after digestion with NotI and AatII was ligated to the 1.928 kb fragment obtained from of p77t-(ura) (SEQ ID NO:45), digested with NotI and AatII.

p77t-(ura)-$P_{PDR5}$-HXT7 (SEQ ID NO:48) (FIG. 11): The 4.723 kb fragment obtained from p77t-(ura)-w/o-prom, by digestion with PstI and SalI, was ligated to the 2.092 kb fragment obtained from pY-$P_{PDR5}$-HXT7 by digestion with XhoI and PstI.

p77t-(ura)-$P_{PDR5long}$-HXT7 (SEQ ID NO: 84) (FIG. 11E): The 8.613 kb fragment obtained from pY-$P_{PDR5}$-HXT7 (SEQ ID NO: 36) by digestion with BamHI and XhoI, was ligated to the 1.188 kb fragment obtained from pSK-$P_{PDR5}$-PPUS (Nakamura et al., Antimicrob. Agents Chemother. 45: 3366-3374 (2001)) (SEQ ID NO: 85) by digestion with BamHI and XhoI.

p77t-(ura)-$P_{CDR1}$-HXT7 (SEQ ID NO:49) (FIG. 11): The 4.723 kb fragment obtained from p77t-(ura)-w/o-prom, by digestion with PstI and SalI, was ligated to the 2.885 kb fragment obtained from pY-$P_{CDR1}$-HXT7, by digestion with XhoI and PstI.

p77t-(ura)-$P_{CDR2}$-HXT7 (SEQ ID NO:50) (FIG. 11): The 4.723 kb fragment obtained from p77t-(ura)-w/o-prom, by digestion with PstI and SalI, was ligated to the 2.633 kb fragment obtained from pY-$P_{CDR2}$-HXT7, by digestion with XhoI and PstI.

p77t-(ura)-$P_{PMA1}$-HXT7 (SEQ ID NO:51) (FIG. 11): The 2.127 kb fragment obtained from pYEX-$P_{PMA1}$-HXT7 (SEQ ID NO:52), by digestion with AgeI and PstI, was ligated to the 5.259 kb fragment obtained from p77t-(ura) (SEQ ID NO:45), by digestion with AgeI and PstI. $P_{PMA1}$ is the yeast promoter of the plasma membrane ATPase PMA1. This promoter is constitutively active in S. cerevisiae.

pYEX-$P_{PMA1}$-HXT7 (SEQ ID NO:52): The PCR product PCR-HXT7 (SEQ ID NO:1) was digested with BamHI and PstI to get a 1.726 kb fragment that subsequently was ligated to the 7.840 kb fragment obtained from pY-$P_{PMA1}$-GFP (SEQ ID NO: 78) after digestion with BamHI and PstI. To obtain pY-$P_{PMA1}$-GFP pYEX-BX-GFP (SEQ ID NO:42) was digested with BamHI and XbaI (completely filled in) to get a 7.831 kb fragment that subsequently was ligated to the 966 bp fragment obtained from pUC18-PMA1 (SEQ ID NO: 79) after digestion with BamHI and EcoRI. To obtain pUC18-PMA1, $P_{PMA1}$ was amplified using the oligonucleotides 5' GAGAGAGCTCCACCGCGGTGGCGGCCAGCTTCCTG AAACGGAGAAACATAAAC (SEQ ID NO:80), positions −908−−935 referring to the coding sequence of PMA1 (NC 001139 Pos. 479915-482671) (SEQ ID NO:83), and 5' TCTCG GATCCTCTAGCGATATTGTTTGATAATTAAATCTTTC (SEQ ID NO: 81), positions −4−−30 referring to the coding sequence of PMA1. Additional nucleotides are typed in italics, restriction sites that were introduced to facilitate cloning (SacI and BamHI, respectively) are underlined, and digested with SacI and BamHI. The resulting 959 bp fragment was subsequently ligated to the 2.672 kb fragment obtained from pUC18 (Fermentas; SEQ ID NO:82) after digestion with SacI and BamHI.

Plasmids Carrying Deletion Cassettes:

pUG6-pre-pdr1 (SEQ ID NO:55): The 3.997 kb fragment obtained from pUG6 (SEQ ID NO:54) (Güldener, U. et al, Nucleic Acids Research 24:2519-2524 (1996)), by digestion with BsiWI and SalI, was ligated to the 0.422 kb fragment obtained from the PCR-product PCR-pre-PDR1 (SEQ ID NO:8), by digestion with BsiWI and SalI.

pUG6-Δpdr1 (SEQ ID NO:53) (FIG. 12): The 4.399 kb fragment obtained from pUG6-pre-pdr1, by digestion with SacII and SpeI, was ligated to the 0.369 kb fragment obtained from the PCR-product PCR-post-PDR1 (SEQ ID NO:12), by digestion with SpeI and SacII.

pUG6-pre-pdr3 (SEQ ID NO:57): The 3.997 kb fragment obtained from pUG6 (SEQ ID NO:54) (Güldener, U. et al, Nucleic Acids Research 24:2519-2524 (1996)), by digestion with BsiWI and SalI was ligated to the 0.326 kb fragment obtained from the PCR-product PCR-pre-PDR3 (SEQ ID NO:15), by digestion with BsiWI and SalI.

pUG6-Δpdr3 (SEQ ID NO:56) (FIG. 12): The 4.251 kb fragment obtained from pUG6-pre-pdr3 (SEQ ID NO:57), by digestion with HpaI and SpeI, was ligated to the 0.404 kb fragment obtained from the PCR-product PCR-post-PDR3 (SEQ ID NO: 19), by digestion with HpaI and SpeI.

Example 2

Construction of Strains

Strains deleted of pdr 1 and/or pdr3:

The disruption cassettes Δpdr1 and Δpdr3 were generated by PCR using the oligo-nucleotides 5'GATCGCGTAATAC-CGGCAATTACGG (SEQ ID NO:58) and 5'GTTTAGCT TTTTTACGTTAGCCTCATAT (SEQ ID NO:59) with pUG6-Δpdr1 as template and 5'ACCGTGCTCTGCT-GCTTTCAGG (SEQ ID NO:60) and 5'CGCAACGGCAG-CAGAATAG AGAAAGC (SEQ ID NO:61) with pUG6-Δpdr3 as template, respectively.

The disruption cassettes Δpdr1 and Δpdr3 were used to transform S. cerevisiae RE700A cells yielding RE700A Δpdr1:: KAN$^r$ and RE700A Δpdr3:: KAN$^r$. The presence of the KAN$^r$-Marker gene flanked by loxP sites (see construction of plasmids) conferred resistance to G418 (250 μg/ml) to RE700A Δpdr1 and RE700A Δpdr3. The KAN$^r$ gene was subsequently removed by cre-recombinase mediated recombination (Güldener, U. et al, Nucleic Acids Research 24:2519-2524 (1996)). RE700A Δpdr1::KAN$^r$ and RE700A Δpdr3::KAN$^r$ were transformed with the cre expression plasmid pSH47 (Güldener, U. et al, Nucleic Acids Research 24:2519-2524 (1996)), which carries the UR43 marker gene and the cre gene under the control of the inducible GAL1 promoter. Expression of the cre recombinase was induced by shifting cells from maltose medium to galactose medium. The cre expression plasmid was removed by streaking cells on plates containing 5-fluoroorotic acid to select for the loss of pSH47, yielding strains RE700A Δpdr1 and RE700A Δpdr3.

To obtain S. cerevisiae strain RE700A Δpdr1,pdr3 the strain RE700A Δpdr1 was transformed with the disruption cassette Δpdr3 yielding RE700A Δpdr1,pdr3::KAN$^r$. RE700A Δpdr1,pdr3:: KAN$^r$ was transformed with the cre expression plasmid pSH47 (Güldener, U. et al, Nucleic Acids Research 24:2519-2524 (1996)). Expression of the cre recombinase was induced by shifting cells from maltose medium to galactose medium. The cre expression plasmid was removed from the strain by streaking cells on plates containing 5-fluoroorotic acid to select for the loss of pSH47, yielding the strain RE700A Δpdr1,pdr3.

Strains episomally expressing HXT7 or GFP:

S. cerevisiae RE700A cells (Reifenberger, E. et al., Molecular Microbiology 16:157-167 (1995)) were transformed using the lithium acetate method (Sambrook, J. et al., Cold Spring Harbour Laboratory Press (1989)) with plasmids pY-$P_{PDR5}$-HXT7, pY-$P_{CDR1}$-HXT7, pY-$P_{CDR2}$-HXT7, pY-$P_{CUP1}$-HXT7, pY-$P_{PDR5}$-GFP, pY-$P_{CDR1}$-GFP, pY-$P_{CDR2}$-GFP yielding strains RE700A e $P_{PDR5}$-HXT7 (ET[PDR]), RE700A e $P_{CDR1}$-HXT7 (ET[CDR1]), RE700A e $P_{CDR2}$-HXT7 (ET[CDR2]), RE700A e $P_{CUP}$-HXT7 (ECFP), RE700A e $P_{PDR5}$-GFP (CQ[PDR]), RE700A e $P_{CDR1}$-GFP (CQ[CDR1]), RE700A e $P_{CDR2}$-GFP (CQ[CDR2]) (Table 1).

S. cerevisiae RE700A Δpdr1, RE700A Δpdr3 and RE700A Δpdr1,pdr3 cells were transformed with the plasmid pY-$P_{PDR5}$-GFP (Table 1) using the lithium acetate method (Sambrook, J. et al., Cold Spring Harbour Laboratory Press (1989)) yielding strains RE700A Δpdr1 [pY-$P_{PDR5}$-GFP], RE700A Δpdr3 [pY-$P_{PDR5}$-GFP], RE700A Δpdr1 Δpdr3 [pY-$P_{PDR5}$-GFP] (Table 1).

Strains chromosomally expressing HXT7: S. cerevisiae RE700A cells were transformed using the lithium acetate method (Sambrook, J. et al., Cold Spring Harbour Laboratory Press (1989)) with linearized (digestion with Not I) plasmids p77t-(ura)-$P_{PDR5}$-HXT7, p77t-(ura)-$P_{CDR1}$-HXT7, p77t-(ura)-$P_{CDR2}$-HXT7 and p77t-(ura)-$P_{PMA1}$-HXT7) yielding the strains RE700A i $P_{PDR5}$-HXT7 (IT[PDR]), RE700A i $P_{CDR1}$-HXT7 (IT[CDR1]), RE700A i $P_{CDR2}$-HXT7 (IT[CDR2]), RE700A i $P_{PMA1}$-HXT7 (ICFP), RE700A Δpdr1 tok1::$P_{PDR5}$-HXT7, RE700A Δpdr3 tok1::$P_{PDR5}$-HXT7, RE700A Δpdr1,pdr3 tok1::$P_{PDR5}$-HXT7 (Table 1).

Verification of Generated Strains:

To prove the presence of the episomally replicating shuttle plasmids in the strains RE700A e $P_{PDR5}$-HXT7 (ET[PDR]), RE700A e $P_{CDR1}$-HXT7 (ET[CDR1]), RE700A e $P_{CDR2}$-HXT7 (ET[CDR2]), RE700A e $P_{PDR5}$-GFP (CQ[PDR]), RE700A e $P_{CDR1}$-GFP (CQ[CDR1]), RE700A e $P_{CDR2}$-GFP (CQ[CDR2]), RE700A e $P_{CUP}$-HXT7 (ECFP), RE700A Δpdr1 [pY-P$_{PDR5}$-GFP], RE700A Δpdr3 [pY-P$_{PDR5}$-GFP] and RE700A Δpdr1 Δpdr3 [pY-P$_{PDR5}$-GFP], plasmid DNAs from these strains were isolated according to standard methods and used to transform *Escherichia coli* XL1-blue cells (Stratagene, La Jolla, USA). Plasmid DNA was isolated from the resulting *E. coli* transformants and analysed by restriction digestion (FIG. 13).

The correct integrations of the replacement cassettes (p77t-(ura)-P$_{PDR5}$-HXT7, p77t-(ura)-P$_{CDR1}$-HXT7, p77t-(ura)-P$_{CDR2}$-HXT7 and p77t-(ura)-P$_{PMA1}$-HXT7) into the tok1 locus were verified by diagnostic PCR. For 5' integration verification the primer 5'AAGAGGGCCGCTGCTCTCTG (SEQ ID NO:62) and 5'AGTTGGGTAACGCCAGGG TTTTCC (SEQ ID NO:63) were used in PCR to amplify a DNA fragment of 770 bp with genomic DNA from generated strains as template. For 3' integration verification the primer 5'GAGGCAGAGAAATTAGCTGG (SEQ ID NO:64) and 5'ACTATACCTATCACGAGTGC (SEQ ID NO: 65) were used in PCR to amplify a 1.402 kb fragment with genomic DNA of generated strains as template (FIG. 14). The analysis verified RE700A i P$_{PDR5}$-HXT7 (IT[PDR]), RE700A i P$_{CDR1}$-HXT7 (IT[CDR$_1$]), RE700A i P$_{CDR2}$-HXT7 (IT[CDR2]), RE700A i P$_{PMA1}$-HXT7 (ICFP), RE700A Δpdr1 tok1::P$_{PDR5}$-HXT7, RE700A Δpdr3 tok1::P$_{PDR5}$-HXT7 and RE700A Δpdr1 Δpdr3 tok1::P$_{PDR5}$-HXT7 (Table 1, FIG. 14).

Southern blot analysis was used to prove the deletion of pdr1 and/or pdr3 in RE700A.

To check the correct disruption of pdr1 in *S. cerevisiae* RE700A and the loss of the Kanamycin gene two digoxigenin-labelled hybridisation probes (pre-pdr1 (SEQ ID NO:66) and post-pdr1 (SEQ ID NO:67)) were generated by PCR in the presence of digoxigenin-dUTP using the primer pairs 5'GATCGCGTAATACCGGCAATTACGG (SEQ ID NO: 68), 5'GAGAGTCGACCTTCCAGTTTCTTGGAT-TCTTTTCTGTATATTC (SEQ ID NO: 69) and 5'CCTCTA-CAGTATCCTGTGGAGCGAC (SEQ ID NO: 70), 5'GTT-TAGCTTTT TTTACGTTAGCCTCATAT (SEQ ID NO:71) respectively. PUG6-Δpdr1 DNA was used as template.

To check the correct disruption of pdr3 in *S. cerevisiae* RE700A and the loss of the Kanamycin gene two digoxigenin-labelled hybridisation probes (pre-pdr3 (SEQ ID NO:72) and post-pdr3 (SEQ ID NO:73)) were generated by PCR in the presence of digoxigenin-dUTP using the primer pairs 5'ACCGTGCTCTGCTGCTTTCAGG (SEQ ID NO: 74); 5'GAGAGTCGACTGCGGTCACGCAATAA-GAAAAAATTAATAAAAC (SEQ ID NO: 75) and 5'GAGAACTAGTAAACGCAAAAGAAATAGG-GAAGCAGAGCATAACC (SEQ ID NO:76), 5'CGCAACG-GCAGCAGAATAGAGAAAGC (SEQ ID NO:77) respectively. PUG6-Δpdr3 DNA was used as template.

Genomic DNA was isolated from RE700A Δpdr1, RE700A Δpdr3 and RE700A Δpdr1,pdr3 was isolated and 1 μg of each DNA was digested with PstI. Another 1 μg of each DNA was digested with BglII. Digested DNAs were separated by agarose gel electrophoresis, blotted on a nylon membrane and cross linked by UV irradiation. The blots were hybridised with the different labelled probes as detailed in Table 2.

TABLE 2

Verification of deletion of pdr1 and pdr3 by Southern blot analysis. Probes and expected length of labelled fragments.

| Probe | genomic DNA digested with | RE700A (expected length of labelled fragment [kb]) | Strains with disrupted gene(s) (expected length of labelled fragment [kb]) |
|---|---|---|---|
| pre-pdr1 | PstI | 1.631 | RE700A ?pdr1 (5.045) |
| post-pdr1 | Bg/II | 10.862 | RE700A ?pdr1 (7.821) |
| pre-pdr3 | PstI | 6.252 | RE700A ?pdr3 (3.394) |
| post-pdr3 | Bg/II | 7.700 | RE700A ?pdr3 (4.842) |
| pre-pdr3 | PstI | | RE700A ?pdr1,pdr3 (3.394) |
| post-pdr3 | Bg/II | | RE700A ?pdr1,pdr3 (4.842) |

After visualisation of the labelled fragments, in all cases the expected signals were obtained (FIG. 15). The analysis verified RE700A Δpdr1, RE700A Δpdr3 and RE700A Δpdr1,pdr3 (Table 1, FIG. 15).

To check the correct integration of P$_{PDR5long}$-HXT7 into the TOK locus of the genome of RE700A, RE700A Δpdr1, RE700A Δpdr3 and RE700A Δpdr1,3 two digoxigenin-labeled hybridisation probes (pre TOK (SEQ ID NO:86) and post TOK (SEQ ID NO: 87)) were generated by PCR in the presence of digoxigenin dUTP using the primer pairs 5'GAGAGGATCCATATATAGAAATCGG-TAAAATAAATACAAG (SEQ ID NO: 88), 5'GAGAGCG-GCCGCCTGCAAATTTATCGAGACTCTG (SEQ ID NO: 89), 5'GAGAGCTAGCAGACTCGAGTGATATA-CAAACACCCGAAGCAT (SEQ ID NO: 90), 5'GAGAGCGGCCGCCGGGATCGATGATCTAGG (SEQ ID NO: 91) respectively. p77t-(ura) (SEQ ID NO: 45) DNA was used as template.

Genomic DNA was isolated from RE700A, RE700A tok1::P$_{PDR5long}$-HXT7, RE700A Δpdr1 tok1::P$_{PDR5long}$-HXT7, RE700A Δpdr3 tok1::P$_{PDR5long}$-HXT7 and RE700A Δpdr1,3 tok::P$_{PDR5long}$-HXT7 and 1 μg of each DNA was digested with PstI. Another 1 μg of each DNA was digested with EcoRV. Digested DNAs were separated by agarose gel electrophoresis, blotted on a nylon membrane and cross-linked by UV irradiation. The blots were hybridised with the different labelled probes as detailed in Table 4.

TABLE 4

Verification of correct integration of P$_{PDR5long}$-HXT7 into the TOK locus of the genome of S. cerevisiae strains by Southern blot analysis. Probes and expected length of labelled fragments.

| yeast strain | hybridisation probe | restriction enzyme | fragment size [kb] |
|---|---|---|---|
| RE700A | pre-tok | EcoRV | 3.050 |
| RE700A | pre-tok | PstI | 4.199 |
| RE700A tok1::P$_{PDR5long}$-HXT7 | pre-tok | PstI | 5.543 |
| RE700A Δpdr1 tok1::P$_{PDR5long}$-HXT7 | pre-tok | PstI | 5.543 |
| RE700A Δpdr3 tok1::P$_{PDR5long}$-HXT7 | pre-tok | PstI | 5.543 |
| RE700A Δpdr1,3 tok1::P$_{PDR5long}$-HXT7 | pre-tok | PstI | 5.543 |
| RE700A tok1::P$_{PDR5long}$-HXT7 | post-tok | EcoRV | 4.464 |
| RE700A Δpdr1 tok1::P$_{PDR5long}$-HXT7 | post-tok | EcoRV | 4.464 |
| RE700A Δpdr3 tok1::P$_{PDR5long}$-HXT7 | post-tok | EcoRV | 4.464 |
| RE700A Δpdr1,3 tok1::P$_{PDR5long}$-HXT7 | post-tok | EcoRV | 4.464 |

After visualisation of the labelled fragments, in all cases the expected signals were obtained (FIG. 16).

31

Example 3

HXT7 Screening System for *S. cerevisiae* MDR Inhibition

The screening system used *Saccharomyces cerevisiae* RE700A, a yeast strain deprived of the seven most important glucose transporters (HXT1-7) (Reifenberger, E. et al., Molecular Microbiology 16:157-167 (1995)). The strain is not able to grow on glucose as the sole carbon source. It grows on maltose (2% (w/v)) as the sole carbon source. In addition, the strain grows well on maltose also in the presence of up to 0.5% (w/v) 2-deoxy-glucose (2-DG), a toxic glucose analogue, in the medium (FIG. 1). Growth is inhibited by 50% at a 2-DG concentration in liquid media of ~1% (w/v) (FIG. 1).

HXT7, encoding Hxt7p, a glucose transporter of *S. cerevisiae*, served as reporter gene. To generate a test strain, HXT7 was introduced into *S. cerevisiae* RE700A under the transcriptional control of a promoter and/or transcription factor that was to be tested.

Construction of a Model Screening System Suitable to Analyse the PDR Network of *S. cerevisiae*:

The multiple drug resistance (MDR) network of *S. cerevisiae* was used to establish a model screening system. The promoter of PDR5 ($P_{PDR5}$) was the target promoter, which in turn can be activated by the transcription factors Pdr1p and Pdr3p that were also included in this screening system.

The strain RE700A was genetically modified, as described in Example 2, expressing episomally (e) or chromosomally (i) the HXT7 gene, encoding the glucose transporter Hxt7p, under the control of the promoter of PDR5, a PDR mediating gene of *S. cerevisiae*, leading to the strains RE700A e $P_{PDR5}$-HXT7 (strain ET[PDR]) and RE700A i $P_{PDR5}$-HXT7 (strain IT[PDR]), respectively. As controls the following strains were generated:

RE700A e $P_{PDR5}$-GFP (strain CQ[PDR]), expressing GFP under control of $P_{PDR5}$, RE700A e $P_{CUP1}$-HXT7 (strain ECFP), expressing the HXT7 gene under the control of the promoter $P_{CUP1}$ and RE700A i $P_{PMA1}$-HXT7 (strain ICFP), expressing the HXT7 gene under the control of the promoter $P_{PMA1}$.

For complete genotypes of all constructed strains refer to Table 1.

Figure 2:
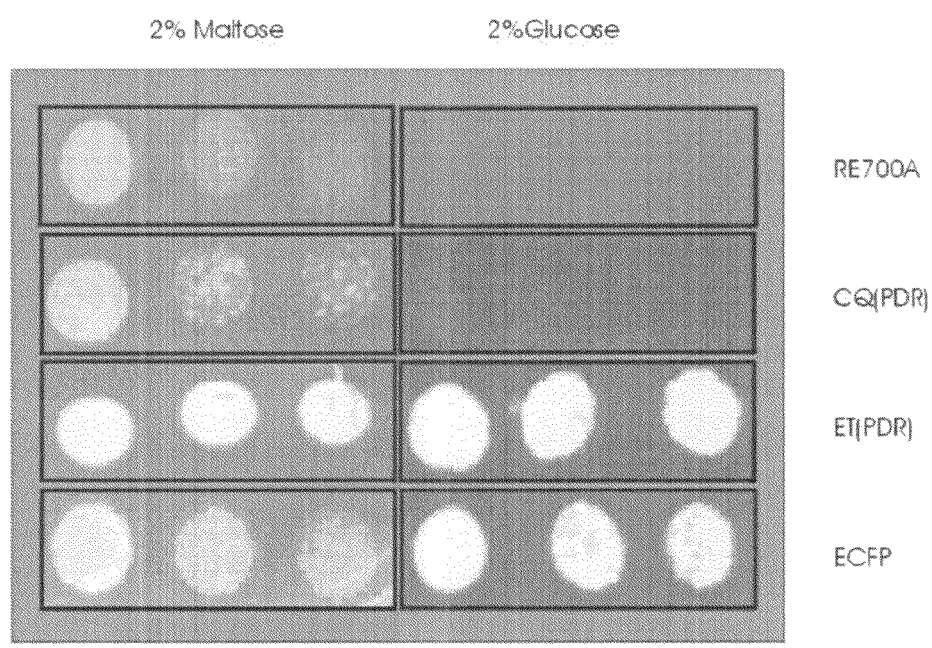
FIG. 2: Growth of RE700A, CQ[PDR], ET[PDR] and ECFP on solid medium for 24 h at 28° C. with 2% (w/v) Maltose and 2% (w/v) Glucose as the carbon source, respectively. In contrast to RE700A and strain CQ[PDR], strain ECFP as well as ET[PDR] are able to grow on 2% (w/v) Glucose as the only carbon source.

In contrast to *S. cerevisiae* strains RE700A and CQ[PDR], the strains ECFP and ET[PDR] were able to grow on 2% (w/v) Glucose as the only carbon source (FIG. 2), indicating the functional expression of HXT7 and the activity of $P_{PDR5}$.

Accordingly, the growth of strains ECFP, ICFP, ET[PDR] and IT[PDR] in liquid media containing maltose as the only carbon source was inhibited by 2-DG at concentrations that did not affect the growth of RE700A and strain CQ[PDR].

Compared to growth of RE700A, growth of ECFP was inhibited by 78% at 0.01% (w/v) 2-DG, by 91% at 0.03% (w/v) 2-DG and by 93% at 0.05% (w/v) 2-DG in liquid medium; growth of ICFP was inhibited by 15% at 0.01% (w/v) 2-DG, for 74% at 0.03% (w/v) 2-DG and by 80% at 0.05% (w/v) 2-DG in liquid medium. Growth of ET[PDR] was inhibited by 87% at 0.01% (w/v) 2-DG, by 94% at 0.03% (w/v) 2-DG and by 96% at 0.05% (w/v) 2-DG in liquid media, growth of IT[PDR] was inhibited by 21% at 0.01% (w/v) 2-DG, by 79% at 0.03% (w/v) 2-DG and by 88% at 0.05% (w/v) 2-DG in liquid medium (FIG. 3).

(1) episomal test system: To screen for inhibitors of the *S. cerevisia* MDR regulatory network the test strain ET[PDR] can be incubated in selective YNB medium with 2% (w/v) maltose as the carbon source and 0.03% (w/v) 2-DG. Under these non-permissive conditions the growth of the test strain ET[PDR] was inhibited when $P_{PDR5}$ was active (FIG. 3).

(2) chromosomal test system: To screen for inhibitors of the *S. cerevisia* MDR regulatory network the test strain IT[PDR] can be incubated in YNB medium with 2% (w/v) maltose as the carbon source and 0.05% (w/v) 2-DG. Under these non-permissive conditions the growth of the test strain IT[PDR] was inhibited when $P_{PDR5}$ was active (FIG. 3).

(3) model system for transcription factor inhibition: Since no specific inhibitors of the *S. cerevisia* MDR network in *S. cerevisiae* are known, the inhibition of two relevant transcription factors, Pdr1 p and Pdr3p, that are known to activate $P_{PDR5}$ was mimicked by their disruption in RE700A, yielding the strains RE700A Δpdr1, RE700A Δpdr3, RE700A Δpdr1,pdr3 (Table 1). These strains were subsequently modified to express HXT7 or GFP under the control of $P_{PDR5}$, yielding strains RE700A Δpdr1 tok1::$P_{PDR5}$-HXT7, RE700A Δpdr3 tok1::$P_{PDR5}$-HXT7, RE700A Δpdr1,pdr3 tok1::$P_{PDR5}$-HXT7, RE700A Δpdr1 [pY-$P_{PDR5}$-GFP], RE700A Δpdr3 [pY-$P_{PDR5}$-GFP], RE700A Δpdr1,pdr3 [pY-$P_{PDR5}$-GFP] (Table 1).

All strains expressing HXT7 were tested for sensitivity to 2-DG. The strains expressing GFP under the control of $P_{PDR5}$ were additionally analysed for GFP fluorescence in comparison to RE700Ae $P_{PDR5}$-GFP (strain CQ[PDR]).

Figure 4:
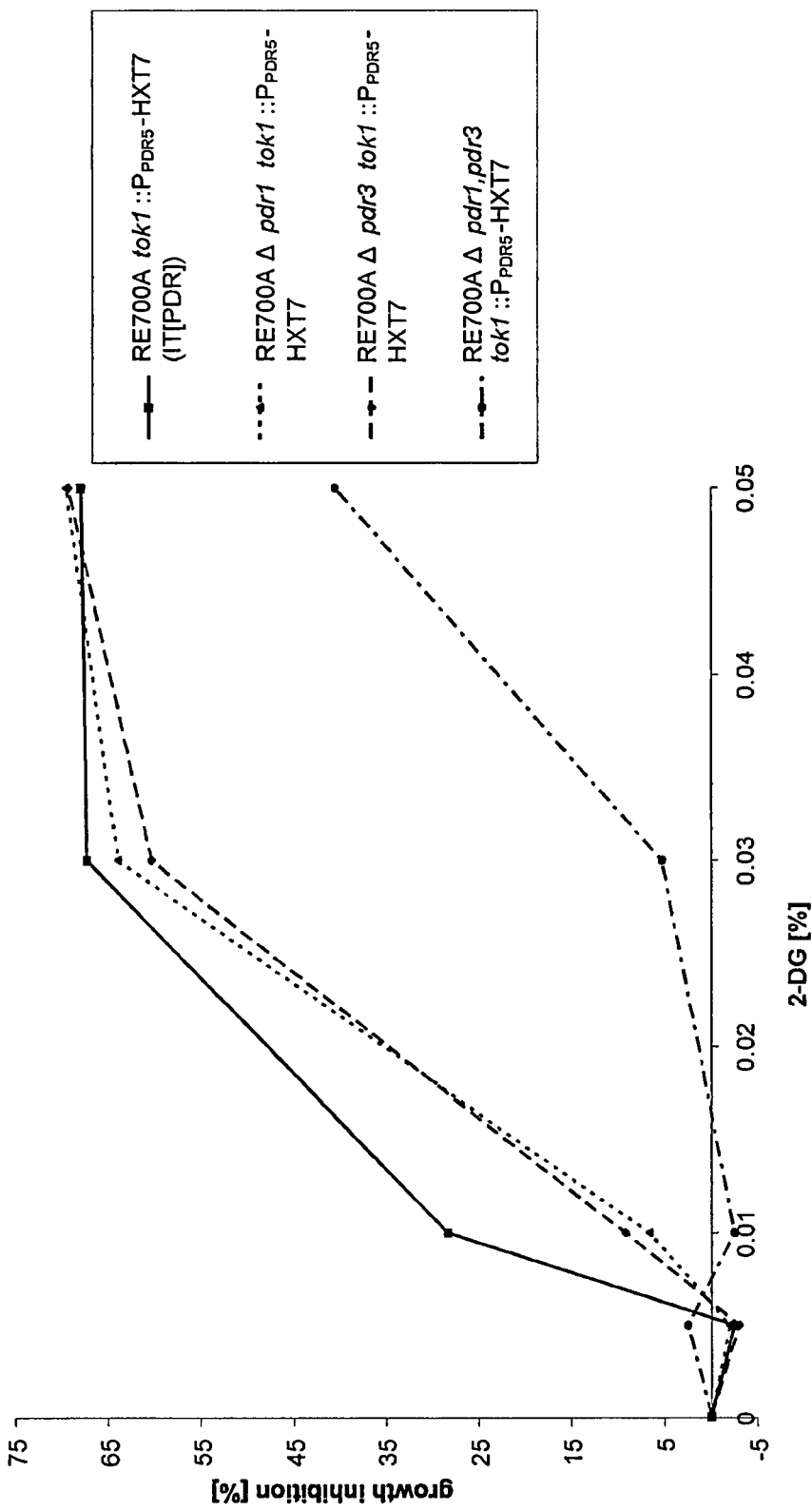
Figure 4:
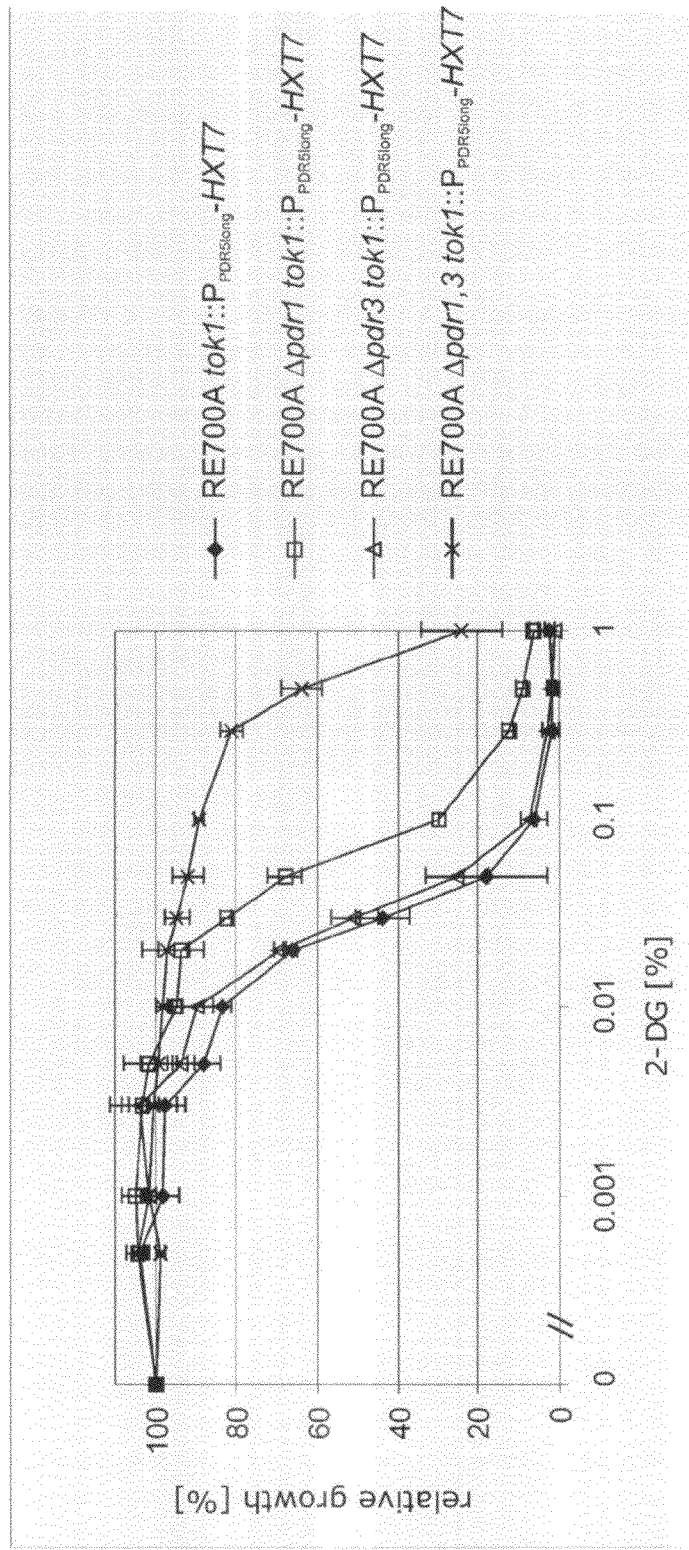

The strain RE700A tok1::$P_{PDR5}$-HXT7 (IT[PDR]) showed 50% growth inhibition at a 2-DG concentration in liquid media of 0.021% (w/v) whereas the strains RE700A Δpdr1 tok1::$P_{PDR5}$-HXT7 and RE700A Δpdr3 tok1::$P_{PDR5}$-HXT7 exhibited 50% growth inhibition at 2-DG concentration of 0.026% (w/v). The strain RE700A Δpdr1,pdr3 tok1::$P_{PDR5}$-HXT7 did not show significant 2-DG sensitivity up to concentrations of 0.03% (w/v) (FIG. 4A).

The strain RE700A tok1::$P_{PDR5long}$-HXT7 showed a 50% growth inhibition at a 2-DG concentration in liquid media of 0,025% (w/v), and is therewith slightly more affected by 2-DG than RE700A Δpdr3 tok1::$P_{PDR5long}$-HXT7 cells, who showed a 50% growth inhibition at 2-DG concentrations of 0.029% (w/v). RE700A Δpdr1 tok1::$P_{PDR5long}$-HXT7 cells were even more resistant to 2-DG with a 50% growth inhibition at a 2-DG concentration of 0.068% (w/v). The tolerance to 2-DG was further increased nearly 10fold in RE700A Δpdr1,3 tok1::$P_{PDR5long}$-HXT7 with a 50% growth inhibition at 2-DG concentrations of 0.6% (w/v) in liquid media (FIG. 4B).

By fluorescence measurement of the strain RE700A [pY-$P_{PDR5}$-GFP] (strain CQ[PDR]) after incubation for 12 h fluorescence of 1000 arbitrary units was determined. By fluorescence measurement of the strain RE700A Δpdr1 [pY-$P_{PDR5}$-GFP] a decreased fluorescence of 350 arbitrary units was detected. By fluorescence measurement of the strain RE700A Δpdr3 [pY-$P_{PDR5}$-GFP] a fluorescence of 750 arbitrary units and by measurement of the strain RE700A Δpdr1,pdr3 [pY-$P_{PDR5}$-GFP] an even more decreased fluorescence of 43 arbitrary units (FIG. 5) were detected.

Example 4

HXT7 Screening System for *Candida albicans* MDR Inhibition

The screening system described in Example 3 was adapted to search for inhibitors of the regulatory elements of *Candida albicans* MDR conferring gene expression, namely the promoters of the *C. albicans* MDR pump genes $CDR_1$ and $CDR_2$ ($P_{CDR1}$ and $P_{CDR2}$).

(1) Episomal screening system for inhibitors of $P_{CDR_1}$: *S. cerevisiae* strain RE700A was transformed with plasmids pY-$P_{CDR1}$-HXT7 and pY-$P_{CDR1}$-GFP yielding strains ET[CDR1] and CQ[CDR1] (for details see Examples 1 and 2, for the complete genotype refer to Table 1). The inhibition of growth of ET[CDR1] by 2-DG was tested. The growth of this strain was inhibited to more than 90% at a 2-DG concentration of 0.05% (w/v) (FIG. 6). To screen for inhibitors of the $P_{CDR1}$, the test strain ET[CDR1] can be incubated in selective YNB medium with 2% (w/v) maltose as the carbon source and 0.05% (w/v) 2-DG. Under these non-permissive conditions the growth of the test strain ET[CDR1] was inhibited when $P_{CDR1}$ was active (FIG. 6).

(2) Episomal screening system for inhibitors of $P_{CDR2}$: *S. cerevisiae* strain RE700A was transformed with plasmids pY-$P_{CDR2}$-HXT7 and pY-$P_{CDR2}$-GFP yielding strains ET[CDR2] and CQ[CDR2] (for details see construction of strains and plasmids, for the complete genotype refer to Table 1). The inhibition of growth of ET[CDR2] by 2-DG was tested. The growth of this strain was inhibited to more than 80% at a 2-DG concentration of 0.2% (w/v) (FIG. 6). To screen for inhibitors of the $P_{CDR2}$, the test strain ET[CDR2] can be incubated in selective YNB medium with 2% (w/v) maltose as the carbon source and 0.2% (w/v) 2-DG. Under these non-permissive conditions the growth of the test strain ET[CDR2] was inhibited when $P_{CDR2}$ was active (FIG. 6).

(3) Integrated screening system for inhibitors of $P_{CDR1}$: *S. cerevisiae* strain RE700A was genetically modified as described in Example 1 and 2 to yield strain IT[CDR1], chromosomally expressing HXT7 under the control of the promoter of CDR1 ($P_{CDR1}$) (for the complete genotype see Table 1). The inhibition of growth of IT[CDR1] by 2-DG was tested. The growth of this strain was inhibited by more than 90% at a 2-DG concentration of 0.03% (w/v) (FIG. 7)

(4) Integrated screening system for inhibitors of $PCDR_2$: *S. cerevisiae* strain RE700A was genetically modified as described in Examples 1 and 2 to yield strain IT[CDR2], chromosomally expressing HXT7 under the control of the promoter of CDR2 ($P_{CDR2}$) (for the complete genotype see Table 1). The inhibition of growth of IT[CDR2] by 2-DG was tested. The growth of this strain was inhibited by 50% at a 2-DG concentration of 1% (w/v) and by 80% at a 2-DG concentration of 2% (w/v) (FIG. 8).

The invention claimed is:

1. A modified yeast strain of the order Saccharomycetales, which is a mutant strain lacking all genes coding for hexose transporters that is transformed with
    a functional nucleic acid segment comprising
        (a) a gene encoding a facultatively lethal reporter protein being a hexose transporter gene which under culture conditions comprising hexose or hexose derivatives gives rise to a lethal phenotype; and
        (b) a promoter controlling the expression of said gene (a) being a promoter controlling the expression of a multiple drug resistance (MDR) conferring gene that is part of a transcriptional regulatory network.

2. The modified yeast strain according to claim 1, which further comprises
    (c) at least one additional gene(s) encoding a transcription factor(s) controlling said promoter (b).

3. The modified yeast strain according to claim 1, wherein the yeast host strain is of the family Saccharomycetaceae.

4. The modified yeast strain according to claim 1, wherein
    (i) the gene encoding the hexose transporter HXT1-7 or Ght1-6; and/or
    (ii) the promoter is a promoter controlling the expression of the MDR conferring gene that is part of the transcriptional regulatory network in pathogens or mammalian tumor cells.

5. The modified yeast strain according to claim 1, wherein the strain is *S. cerevisiae* RE700A comprising HXT7 as reporter gene under the control of a promoter of a MDR conferring gene.

6. The modified yeast strain selected from the strains listed in Table 1 wherein the strain is *S. cerevisiae* RE700A comprising HXT7 as reporter gene under the control of a promoter of a MDR conferring gene.

7. The modified yeast strain of claim 1, wherein the lethal phenotype is induced by a defined concentration of hexose or hexose derivative in the growth medium.

8. An integration vector comprising a functional nucleic acid segment as defined in claim 1.

9. The integration vector of claim 8, which is suitable for chromosomal integration and wherein the functional nucleic acid segment is flanked by sequences homologous to the target site DNA sequences in the host strain.

10. Kit for the identification of inhibitors of transcription factors and/or gene promoters within a transcriptional regulatory network by a positive phenotype using a genetically modified yeast strain, said kit comprising
    (i) a modified yeast strain according to claim 1; or
    (ii) an integration vector according to claim 19.

11. The kit of claim 10 further comprising
    (iii) a comparative yeast strain in which the promoter is a constitutively active promoter; wherein the comparative yeast strain is a mutant strain lacking genes coding for all hexose transporters that is transformed with a functional nucleic acid segment comprising a gene encoding a facultatively lethal reporter protein being a hexose transporter gene which under culture conditions comprising hexose or hexose derivatives gives rise to a lethal phenotype; and/or
    (iv) culture media for (i) and/or (iii).

12. The modified yeast strain of claim 1, wherein the mutant yeast strain lacking hexose transporters lacks glucose transporters.

13. The modified yeast strain of claim 12, wherein the mutant yeast strain is the *S. cerevisiae* mutant RE700A (MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3).

14. The modified yeast of claim 1, wherein the *S. cerevisiae* promoter is a promoter of the PDR gene family, and wherein the human pathogenic yeast promoter is a promoter from *Candida* spp.

15. The modified yeast of claim 14, wherein the promoter of the PDR gene family is *S. cerevisiae* PDR5-promoter ($P_{PDR5}$) and wherein the human pathogenic yeast promoter is a promoter from *C. albicans*.

16. The modified yeast of claim 15, wherein the *C. albicans* promoter is the *C. albicans* CDR1-promoter $P_{CDR1}$ or the *C. albicans* CDR2-promoter $P_{CDR2}$.

17. The modified yeast of claim 1, wherein one of the genes encoding the hexose transporter is *S. cerevisiae* HXT7.

18. The modified yeast strain of claim 6, wherein the modified yeast strain is selected from the group consisting of RE700A e $P_{PDR5}$-HXT7, RE700A e $P_{CDR1}$-HXT7, RE700A e $P_{CDR2}$-HXT7, RE700A e $P_{CUP}$-HXT7, RE700A i $P_{PDR5}$-HXT7, RE700A i $P_{CDR1}$-HXT7, RE700A Δpdr1 tok1::$P_{PDR5}$-HXT7, RE700A Δpdr3 tok1::$P_{PDR5}$-HXT7, and RE700A Δpdr1 Δpdr3 tok1::$P_{PDR5}$-HXT7.

19. The modified yeast strain of claim 18, wherein the modified yeast strain is RE700A i $P_{PDR5}$-HXT7 (MATa ura3-52 his3-11,15 lue2-3,112 MAL2 SUC2 GAL MEL hxt1Δ::HIS3::Δhxt4 hxt5::LEU2 hxt2Δ::HIS3 hxt3Δ::LEU2::Δhxt6 hxt7::HIS3 tok1::$P_{PDR5}$HXT7) deposited as DSM 16852.

20. The modified yeast strain of claim 7, wherein the lethal phenotype is induced by a defined concentration of 2-deoxyglucose.

21. The modified yeast strain of claim 3, wherein the yeast host strain of the family Saccharomycetaceae is *S. cerevisiae*.

* * * * *